United States Patent
Kreps et al.

(10) Patent No.: US 7,186,887 B2
(45) Date of Patent: Mar. 6, 2007

(54) NUCLEIC ACIDS ENCODING ORYZA SATIVA NUCLEAR CAP BINDING PROTEIN 80 AND METHODS OF USE

(75) Inventors: Joel Kreps, Carlsbad, CA (US); Pamela S. Nero, Philadelphia, PA (US)

(73) Assignee: Syngenta Participations AG, Basel (CH)

( * ) Notice: Subject to any disclaimer, the term of this patent is extended or adjusted under 35 U.S.C. 154(b) by 381 days.

(21) Appl. No.: 10/469,013

(22) PCT Filed: Apr. 5, 2002

(86) PCT No.: PCT/EP02/03809

§ 371 (c)(1),
(2), (4) Date: Aug. 26, 2003

(87) PCT Pub. No.: WO02/081696

PCT Pub. Date: Oct. 17, 2002

(65) Prior Publication Data

US 2004/0096861 A1    May 20, 2004

Related U.S. Application Data

(60) Provisional application No. 60/282,370, filed on Apr. 6, 2001.

(51) Int. Cl.
  *C12N 15/82* (2006.01)
  *A01H 5/00* (2006.01)
  *C07H 21/04* (2006.01)

(52) U.S. Cl. .................. 800/286; 800/320.2; 800/285; 435/468; 435/419; 435/320.1; 536/24.5; 536/23.6; 536/23.1

(58) Field of Classification Search ..................... None
See application file for complete search history.

(56) References Cited

U.S. PATENT DOCUMENTS 5,702,933 A * 12/1997 Klee et al. ................. 800/283
2004/0123343 A1* 6/2004 La Rosa et al. ............ 800/278

FOREIGN PATENT DOCUMENTS

WO    WO9906580    2/1999
WO    WO0196585    12/2001

OTHER PUBLICATIONS

Derba M, Kmieciak M, and Jarmolowski A. Molecular Characterization of Oryza sativa CBP80 (Jan. 31, 2001) GenBank Accession AY017415.*
Kmieciak et al., Arabidopsis thaliana nuclear cap-binding protein CBP80 mRNA, complete cds; Database EMBL Sequence Database, Jun. 23, 2000, Accession No. AF268377.*
Marintchev et al. eIF4G and CBP80 share a common origin and similar domain organization: implications for the structure and function of eIF4G.(2005) Biochemistry, vol. 44, pp. 12265-12272.*
Pathan et al. Subtracted rice IR62266 leaf drought-stressed cDNA library. (2004) GenBank Accession No. CK738450, pp. 1-2.*
Lazar et al. Transforming Growth Factor alpha: mutation of aspartic acid 47 and leucine 48 results in different biological activities. (1988) Molecular and Cellular Biology, vol. 8, pp. 1247-1252.*
Hill et al. Functional analysis of conserved histidines in ADP-glucose pyrophosphorylase from *Escherichia coli*. (1998) Biochemical and Biophysical Research Communications, vol. 244, pp. 573-577.*
Guo et al. Protein tolerance to random amino acid change. (2004) PNAS, vol. 101, pp. 9205-9210.*
Derba et al. Molecular characterization of Oryza sativa CBP80 (2001) GenBank Accession No. AY017415, pp. 1-3.*
Elomaa et al. Transformation of antisense constructs of the chalcone synthase gene superfamily into *Gerbera hybrida*: differential effect on the expression of family members. (1996) Molecular Breeding, vol. 2, pp. 41-50.*
Colliver et al. Differential modification of flavonoid and isoflavonoid biosynthesis with an antisense chalcone synthase construct in transgenic lotus corniculatus. (1997) PMB, vol. 35, pp. 509-522.*
Derba et al, *Oryza sativa subsp. Japonica nuclear cap-binding protein CBP80 mRNA, complete cds* Database EMBL Sequence Database [online], (Jan. 31, 2001), Accession No. AY017415.
Hugouvieux et al, *An mRNA cap binding protein, ABH1, modulates early abscisic acid signal transduction in Arabidopsis Cell*, vol. 106, No. 4 (Aug. 24, 2001), pp. 477-487.

* cited by examiner

*Primary Examiner*—Medina A. Ibrahim
*Assistant Examiner*—Cathy Kingdon Worley
(74) *Attorney, Agent, or Firm*—Syngenta Biotechnology

(57) ABSTRACT

An isolated polynucleotide encoding a full-length rice cap binding protein 80 (CBP80) is provided. The reduction in expression or activity of CBP80 in a transgenic rice plant cell may be accomplished by antisense sequences which can inhibit expression or activity of endogenous CBP80 in a rice plant cell which may lead to alterations in hormone signaling.

13 Claims, No Drawings

SEQUENCE LISTING

```
<160> NUMBER OF SEQ ID NOS: 54

<210> SEQ ID NO 1
<211> LENGTH: 2985
<212> TYPE: DNA
<213> ORGANISM: Oryza sativa

<400> SEQUENCE: 1
cgaacccgac gagtatcccg accaccactc tctctctctc tctactctcc ctcctcgccg     60
cgccgcgccg ccgccgccgc catgagcgcg ggctggagga cgctgctgct gcggatcggc    120
gacaggtgcc cggagtacgg gggctccgcc gaccacaagg agcacatcga aacttgttat    180
```

-continued

| | | | | |
|---|---|---|---|---|
| ggtgtgcttt | gtcgagaata | cgaacactcc | aaagatgcaa | tgtttgagtt tctcctccaa | 240 |
| tgtgcagatc | aattgcctca | caagattcct | ttctttggag | tattgatagg tttgataaac | 300 |
| ttggaaaatg | aagatttttc | caagggtatt | gtcgatacaa | cacatgccaa tttacaggat | 360 |
| gccttgcata | atgaaaatcg | tgacagaatc | aggatattgc | tgcgatttct ctgtggcctg | 420 |
| atgtgcagca | aagttgtcct | gccaaattct | attattgaaa | catttgaggc actattatca | 480 |
| tctgctgcaa | caatattaga | tgaggaaacc | ggaaatcctt | cgtggcaacc acgtgctgat | 540 |
| ttctatgttt | attgtatctt | ggcttccctt | ccatggggtg | gctcagaatt gtttgagcaa | 600 |
| gttccagatg | aatttgagag | agttctggtt | ggtatacagt | cttatataag cattagaagg | 660 |
| cattttgatg | atattgcttt | ctcagtcttt | gaaacagatg | aaggcaactc tcccaacaaa | 720 |
| aaggatttca | tcgaagattt | atgggagcgt | attcaagttc | tttctcgcaa tgggtggaag | 780 |
| gttaagagtg | ttccaaaacc | tcacctgtcg | tttgaagctc | agctggtagc tggagtttct | 840 |
| caccgtttct | ccccaattag | ttgccccccca | cctactatct | cgcaatcatc ttctgaaata | 900 |
| gtaaaaggtc | aagaaaagca | tgaagctgat | ctgaagtatc | ctcaaaggct tcgtaggctt | 960 |
| cacatatttc | caacaaataa | agctgagaac | atgcaacctg | tagatcgttt tgttgttgaa | 1020 |
| gaatgcatat | tggatgtgct | acttttcttc | aatggatgtc | gcaaagaatg tgcattttat | 1080 |
| ctggtcagct | tacctgtgcc | tttccgttat | gaatacctga | tggctgagac catattttca | 1140 |
| cagctactgt | tattgccgaa | tccccctttc | aggccaattt | actataccct ggttattatc | 1200 |
| gaccttgcca | aggcattgcc | aggtgcattt | ccttcagttg | tggtaggagc agtacatgct | 1260 |
| cttttttgaca | gaattagcaa | catggatatg | gagtgccgca | cccgacttat cctatggttt | 1320 |
| tcacatcact | tgtcaaattt | tcagttcatt | tggccttggc | aggagtgggc ttacgtcaag | 1380 |
| gaccttccaa | aatgggctcc | acagcgtgtt | tttgtccaag | aagtattaga aagggaaatt | 1440 |
| cgcttgtcct | actttgacaa | aattaagcag | agcatagagg | atgctgttga attggaagaa | 1500 |
| ctgttacccc | caaaagctgg | gcctaacttc | agatatcata | gtgatgaagg caaagaaagc | 1560 |
| actgatggcc | acagactctc | caaggaactt | gttgccatgg | ttagaggaag gaagacacaa | 1620 |
| ggtgatatta | tttcatgggt | agacgaaaaa | ataattcctg | taaatggtgc caaatttgca | 1680 |
| cttgatgtag | ttagccagac | acttctggac | attggctcaa | aaagtttcac ccatcttatc | 1740 |
| actgttttgg | agagatatgg | tcaaataata | tcaaagctgt | gcccgaatga agaaatgcag | 1800 |
| ttattgttga | tggatgaagt | cagtgcttat | tggaagaaca | gtacccagat gattgccata | 1860 |
| gctattgata | ggatgatggg | ttatcgccta | ctttccaatc | tggctatagt caaatgggtt | 1920 |
| ttttctcctg | ctaatgttga | tcaatttcat | gtttcagatc | gtccatggga gattcttaga | 1980 |
| aatgctgtta | gtaaaacata | caatcggatt | tttgacctcc | ggaaagaaat tcagacactc | 2040 |
| aggaaaggtc | ttcaagctgc | taaagaggcc | agtgaaaagg | ccgccagaga gttggaggag | 2100 |
| gctaaatcta | ttattgagat | tgtagatggc | caacctgtgc | catctgaaaa tccaggaagg | 2160 |
| ctaagacgac | ttcaagcgcg | tgctgacaaa | gcgaagaag | gagaagtaac cactgaagaa | 2220 |
| tctttagaag | caaggaggc | cctccttgct | cgagggcttg | aagaaagcaa ggaattgctt | 2280 |
| aggttactat | tcaagagctt | tgttgaagtg | ctaactgaac | gtttgccacc tatttctgct | 2340 |
| gatggagatg | ttcctaattt | acgtgctgga | gacccgaatg | taaattcttc agcccgtgac | 2400 |
| cctgaagcaa | caaccatgga | aatagacaat | gaaaatggag | gagataacga tagcagtcag | 2460 |
| ctgaatggtc | aaaacaagaa | aatcagtcac | aatgttggag | agcttgagca atggtgtctc | 2520 |
| tgcacattgg | gctatctcaa | gtcgtttttct | cgtcaatatg | ctactgagat ctggtcccat | 2580 |

-continued

```
attgccatgt tggatcagga gattttcgtt gggaatattc accctcttat ccggaaagct    2640
gctttctccg gtttgtgcag acctaccagt gaagggtctc acctttgatt ttgacccttc    2700
cagtgagttg gagtttacct gtattatacg cgacaaattt ttcatcatgc ttcactaact    2760
ggacatgccc aaaagtactc tgatgtgtac tcaggaactc catcgattct cctgtaatcc    2820 tgccccgag gaacacccttt ggtggaaagc actgtaacga ctttaggtga ttaaattatc    2880
agttaggttt atttgaattg tagtggacta attttcttgg gtgagtaatt gctatggtct    2940
agctttctta attccctctg cctgtgttag gacaacgccg tgttt                   2985
```

```
<210> SEQ ID NO 2
<211> LENGTH: 868
<212> TYPE: PRT
<213> ORGANISM: Oryza sativa

<400> SEQUENCE: 2
```

| | | | | | | | | | | | | | | |
|---|---|---|---|---|---|---|---|---|---|---|---|---|---|---|
| Met | Ser | Ala | Gly | Trp | Arg | Thr | Leu | Leu | Leu | Arg | Ile | Gly | Asp | Arg | Cys |
| 1 | | | | 5 | | | | | 10 | | | | | 15 | |

Pro Glu Tyr Gly Gly Ser Ala Asp His Lys Glu His Ile Glu Thr Cys
            20                  25                  30

Tyr Gly Val Leu Cys Arg Glu Tyr Glu His Ser Lys Asp Ala Met Phe
        35                  40                  45

Glu Phe Leu Leu Gln Cys Ala Asp Gln Leu Pro His Lys Ile Pro Phe
    50                  55                  60

Phe Gly Val Leu Ile Gly Leu Ile Asn Leu Glu Asn Glu Asp Phe Ser
65                  70                  75                  80

Lys Gly Ile Val Asp Thr Thr His Ala Asn Leu Gln Asp Ala Leu His
                85                  90                  95

Asn Glu Asn Arg Asp Arg Ile Arg Ile Leu Leu Arg Phe Leu Cys Gly
            100                 105                 110

Leu Met Cys Ser Lys Val Val Leu Pro Asn Ser Ile Ile Glu Thr Phe
        115                 120                 125

Glu Ala Leu Leu Ser Ser Ala Ala Thr Ile Leu Asp Glu Glu Thr Gly
    130                 135                 140

Asn Pro Ser Trp Gln Pro Arg Ala Asp Phe Tyr Val Tyr Cys Ile Leu
145                 150                 155                 160

Ala Ser Leu Pro Trp Gly Gly Ser Glu Leu Phe Glu Gln Val Pro Asp
                165                 170                 175

Glu Phe Glu Arg Val Leu Val Gly Ile Gln Ser Tyr Ile Ser Ile Arg
            180                 185                 190

Arg His Phe Asp Asp Ile Ala Phe Ser Val Phe Glu Thr Asp Glu Gly
        195                 200                 205

Asn Ser Pro Asn Lys Lys Asp Phe Ile Glu Asp Leu Trp Glu Arg Ile
    210                 215                 220

Gln Val Leu Ser Arg Asn Gly Trp Lys Val Lys Ser Val Pro Lys Pro
225                 230                 235                 240

His Leu Ser Phe Glu Ala Gln Leu Val Ala Gly Val Ser His Arg Phe
                245                 250                 255

Ser Pro Ile Ser Cys Pro Pro Thr Ile Ser Gln Ser Ser Glu
            260                 265                 270

Ile Val Lys Gly Gln Glu Lys His Glu Ala Asp Leu Lys Tyr Pro Gln
        275                 280                 285

Arg Leu Arg Arg Leu His Ile Phe Pro Thr Asn Lys Ala Glu Asn Met
    290                 295                 300

-continued

```
Gln Pro Val Asp Arg Phe Val Glu Glu Cys Ile Leu Asp Val Leu
305                 310                 315                 320

Leu Phe Phe Asn Gly Cys Arg Lys Glu Cys Ala Phe Tyr Leu Val Ser
                325                 330                 335

Leu Pro Val Pro Phe Arg Tyr Glu Tyr Leu Met Ala Glu Thr Ile Phe
            340                 345                 350

Ser Gln Leu Leu Leu Leu Pro Asn Pro Pro Phe Arg Pro Ile Tyr Tyr
        355                 360                 365

Thr Leu Val Ile Ile Asp Leu Cys Lys Ala Leu Pro Gly Ala Phe Pro
    370                 375                 380

Ser Val Val Val Gly Ala Val His Ala Leu Phe Asp Arg Ile Ser Asn
385                 390                 395                 400

Met Asp Met Glu Cys Arg Thr Arg Leu Ile Leu Trp Phe Ser His His
                405                 410                 415

Leu Ser Asn Phe Gln Phe Ile Trp Pro Trp Gln Glu Trp Ala Tyr Val
            420                 425                 430

Lys Asp Leu Pro Lys Trp Ala Pro Gln Arg Val Phe Val Gln Glu Val
        435                 440                 445

Leu Glu Arg Glu Ile Arg Leu Ser Tyr Phe Asp Lys Ile Lys Gln Ser
    450                 455                 460

Ile Glu Asp Ala Val Glu Leu Glu Glu Leu Leu Pro Pro Lys Ala Gly
465                 470                 475                 480

Pro Asn Phe Arg Tyr His Ser Asp Gly Lys Glu Ser Thr Asp Gly
                485                 490                 495

His Arg Leu Ser Lys Glu Leu Val Ala Met Val Arg Gly Arg Lys Thr
            500                 505                 510

Gln Gly Asp Ile Ile Ser Trp Val Asp Glu Lys Ile Ile Pro Val Asn
        515                 520                 525

Gly Ala Lys Phe Ala Leu Asp Val Val Ser Gln Thr Leu Leu Asp Ile
    530                 535                 540

Gly Ser Lys Ser Phe Thr His Leu Ile Thr Val Leu Glu Arg Tyr Gly
545                 550                 555                 560

Gln Ile Ile Ser Lys Leu Cys Pro Asn Glu Glu Met Gln Leu Leu Leu
                565                 570                 575

Met Asp Glu Val Ser Ala Tyr Trp Lys Asn Ser Thr Gln Met Ile Ala
            580                 585                 590

Ile Ala Ile Asp Arg Met Met Gly Tyr Arg Leu Leu Ser Asn Leu Ala
        595                 600                 605

Ile Val Lys Trp Val Phe Ser Pro Ala Asn Val Asp Gln Phe His Val
    610                 615                 620

Ser Asp Arg Pro Trp Glu Ile Leu Arg Asn Ala Val Ser Lys Thr Tyr
625                 630                 635                 640

Asn Arg Ile Phe Asp Leu Arg Lys Glu Ile Gln Thr Leu Arg Lys Gly
                645                 650                 655

Leu Gln Ala Ala Lys Glu Ala Ser Glu Lys Ala Ala Arg Glu Leu Glu
            660                 665                 670

Glu Ala Lys Ser Ile Ile Glu Ile Val Asp Gly Gln Pro Val Pro Ser
        675                 680                 685

Glu Asn Pro Gly Arg Leu Arg Arg Leu Gln Ala Arg Ala Asp Lys Ala
    690                 695                 700

Lys Glu Gly Glu Val Thr Thr Glu Glu Ser Leu Glu Ala Lys Glu Ala
705                 710                 715                 720
```

-continued

```
Leu Leu Ala Arg Gly Leu Glu Glu Ser Lys Glu Leu Arg Leu Leu
            725                 730                 735

Phe Lys Ser Phe Val Glu Val Leu Thr Glu Arg Leu Pro Pro Ile Ser
            740                 745                 750

Ala Asp Gly Asp Val Pro Asn Leu Arg Ala Gly Asp Pro Asn Val Asn
                755                 760                 765

Ser Ser Ala Arg Asp Pro Glu Ala Thr Thr Met Glu Ile Asp Asn Glu
770                 775                 780

Asn Gly Gly Asp Asn Asp Ser Ser Gln Leu Asn Gly Gln Asn Lys Lys
785                 790                 795                 800

Ile Ser His Asn Val Gly Glu Leu Glu Gln Trp Cys Leu Cys Thr Leu
                805                 810                 815

Gly Tyr Leu Lys Ser Phe Ser Arg Gln Tyr Ala Thr Glu Ile Trp Ser
            820                 825                 830

His Ile Ala Met Leu Asp Gln Glu Ile Phe Val Gly Asn Ile His Pro
        835                 840                 845

Leu Ile Arg Lys Ala Ala Phe Ser Gly Leu Cys Arg Pro Thr Ser Glu
    850                 855                 860

Gly Ser His Leu
865

<210> SEQ ID NO 3
<211> LENGTH: 26
<212> TYPE: DNA
<213> ORGANISM: Oryza sativa

<400> SEQUENCE: 3
tgctgctgcg gatcggcgac aggtgc                                        26

<210> SEQ ID NO 4
<211> LENGTH: 24
<212> TYPE: DNA
<213> ORGANISM: Oryza sativa

<400> SEQUENCE: 4
tccgccgacc acaaggagca catt                                          24

<210> SEQ ID NO 5
<211> LENGTH: 29
<212> TYPE: DNA
<213> ORGANISM: Oryza sativa

<400> SEQUENCE: 5
ctgctgcaac aatattagat gaggaaacc                                     29

<210> SEQ ID NO 6
<211> LENGTH: 32
<212> TYPE: DNA
<213> ORGANISM: Oryza sativa

<400> SEQUENCE: 6
ttctatgttt attgtatctt ggcttccctt cc                                 32

<210> SEQ ID NO 7
<211> LENGTH: 32
<212> TYPE: DNA
<213> ORGANISM: Oryza sativa

<400> SEQUENCE: 7
ggaagggaag ccaagataca ataaacatag aa                                 32
```

```
<210> SEQ ID NO 8
<211> LENGTH: 30
<212> TYPE: DNA
<213> ORGANISM: Oryza sativa

<400> SEQUENCE: 8
cccccaccta ctatctcgca atcatcttct                                    30

<210> SEQ ID NO 9
<211> LENGTH: 30
<212> TYPE: DNA
<213> ORGANISM: Oryza sativa

<400> SEQUENCE: 9
aggcttcgta ggcttcacat atttccaaca                                    30

<210> SEQ ID NO 10
<211> LENGTH: 32
<212> TYPE: DNA
<213> ORGANISM: Oryza sativa

<400> SEQUENCE: 10
gctaccagct gagcttcaaa cgacaggtga gg                                 32

<210> SEQ ID NO 11
<211> LENGTH: 34
<212> TYPE: DNA
<213> ORGANISM: Oryza sativa

<400> SEQUENCE: 11
tgttggaaat atgtgaagcc tacgaagcct ttga                               34

<210> SEQ ID NO 12
<211> LENGTH: 31
<212> TYPE: DNA
<213> ORGANISM: Oryza sativa

<400> SEQUENCE: 12
ggacattggc tcaaaaagtt tcacccatct t                                  31

<210> SEQ ID NO 13
<211> LENGTH: 34
<212> TYPE: DNA
<213> ORGANISM: Oryza sativa

<400> SEQUENCE: 13
ttgatggatg aagtcagtgc ttattggaag aaca                               34

<210> SEQ ID NO 14
<211> LENGTH: 25
<212> TYPE: DNA
<213> ORGANISM: Oryza sativa

<400> SEQUENCE: 14
gggctccaca gcgtgttttt gtcca                                         25

<210> SEQ ID NO 15
<211> LENGTH: 34
<212> TYPE: DNA
<213> ORGANISM: Oryza sativa

<400> SEQUENCE: 15
ttctaatact tcttggacaa aaacacgctg tgga                               34
```

```
<210> SEQ ID NO 16
<211> LENGTH: 34
<212> TYPE: DNA
<213> ORGANISM: Oryza sativa

<400> SEQUENCE: 16
taacagttct tccaattcaa cagcatcctc tatg                                    34

<210> SEQ ID NO 17
<211> LENGTH: 33
<212> TYPE: DNA
<213> ORGANISM: Oryza sativa

<400> SEQUENCE: 17
ctgggtactg ttcttccaat aagcactgac ttc                                     33

<210> SEQ ID NO 18
<211> LENGTH: 848
<212> TYPE: PRT
<213> ORGANISM: Arabidopsis thaliana

<400> SEQUENCE: 18
```

Met Ser Asn Trp Lys Thr Leu Leu Arg Ile Gly Glu Lys Gly Pro
 1               5                  10                  15

Glu Tyr Gly Thr Ser Ser Asp Tyr Lys Asp His Ile Glu Thr Cys Phe
                20                  25                  30

Gly Val Ile Arg Arg Glu Ile Glu Arg Ser Gly Asp Gln Val Leu Pro
                35                  40                  45

Phe Leu Leu Gln Cys Ala Glu Gln Leu Pro His Lys Ile Pro Leu Tyr
        50                  55                  60

Gly Thr Leu Ile Gly Leu Leu Asn Leu Glu Asn Glu Asp Phe Val Gln
65                  70                  75                  80

Lys Leu Val Glu Ser Val His Ala Asn Phe Gln Val Ala Leu Asp Ser
                85                  90                  95

Gly Asn Cys Asn Ser Ile Arg Ile Leu Leu Arg Phe Met Thr Ser Leu
                100                 105                 110

Leu Cys Ser Lys Val Ile Gln Pro Ala Ser Leu Ile Val Val Phe Glu
            115                 120                 125

Thr Leu Leu Ser Ser Ala Ala Thr Thr Val Asp Glu Glu Lys Gly Asn
        130                 135                 140

Pro Ser Trp Gln Pro Gln Ala Asp Phe Tyr Val Ile Cys Ile Leu Ser
145                 150                 155                 160

Ser Leu Pro Trp Gly Gly Ser Glu Leu Ala Glu Gln Val Pro Asp Glu
                165                 170                 175

Ile Glu Arg Val Leu Val Gly Ile Gln Ala Tyr Leu Ser Ile Arg Lys
                180                 185                 190

Asn Ser Ser Thr Ser Gly Leu Asn Phe Phe His Asn Gly Glu Phe Glu
            195                 200                 205

Ser Ser Leu Ala Glu Lys Asp Phe Val Glu Asp Leu Leu Asp Arg Ile
        210                 215                 220

Gln Ser Leu Ala Ser Asn Gly Trp Lys Leu Glu Ser Val Pro Arg Pro
225                 230                 235                 240

His Leu Ser Phe Glu Ala Gln Leu Val Ala Gly Lys Phe His Glu Leu
                245                 250                 255

Arg Pro Ile Lys Cys Met Glu Gln Pro Ser Pro Ser Asp His Ser
                260                 265                 270

```
Arg Ala Tyr Ser Gly Lys Gln Lys His Asp Ala Leu Thr Arg Tyr Pro
        275                 280                 285

Gln Arg Ile Arg Arg Leu Asn Ile Phe Pro Ala Asn Lys Met Glu Asp
    290                 295                 300

Val Gln Pro Ile Asp Arg Phe Val Val Glu Glu Tyr Leu Leu Asp Val
305                 310                 315                 320

Leu Phe Tyr Leu Asn Gly Cys Arg Lys Glu Cys Ala Ser Tyr Met Ala
                325                 330                 335

Asn Leu Pro Val Thr Phe Arg Tyr Glu Tyr Leu Met Ala Glu Thr Leu
            340                 345                 350

Phe Ser Gln Ile Leu Leu Pro Gln Pro Pro Phe Lys Thr Leu Tyr
        355                 360                 365

Tyr Thr Leu Val Ile Met Asp Leu Cys Lys Ala Leu Pro Gly Ala Phe
    370                 375                 380

Pro Ala Val Val Ala Gly Ala Val Arg Ala Leu Phe Glu Lys Ile Ser
385                 390                 395                 400

Asp Leu Asp Met Glu Ser Arg Thr Arg Leu Ile Leu Trp Phe Ser His
                405                 410                 415

His Leu Ser Asn Phe Gln Phe Ile Trp Pro Trp Glu Glu Trp Ala Phe
            420                 425                 430

Val Leu Asp Leu Pro Lys Trp Ala Pro Lys Arg Val Phe Val Gln Glu
        435                 440                 445

Ile Leu Gln Arg Glu Val Arg Leu Ser Tyr Trp Asp Lys Ile Lys Gln
    450                 455                 460

Ser Ile Glu Asn Ala Thr Ala Leu Glu Glu Leu Leu Pro Pro Lys Ala
465                 470                 475                 480

Gly Pro Asn Phe Met Tyr Ser Leu Glu Glu Gly Lys Glu Lys Thr Glu
                485                 490                 495

Glu Gln Gln Leu Ser Ala Glu Leu Ser Arg Lys Val Lys Glu Lys Gln
            500                 505                 510

Thr Ala Arg Asp Met Ile Val Trp Ile Glu Glu Thr Ile Tyr Pro Val
        515                 520                 525

His Gly Phe Glu Val Thr Leu Thr Ile Val Gln Thr Leu Leu Asp
    530                 535                 540

Ile Gly Ser Lys Ser Phe Thr His Leu Val Thr Val Leu Glu Arg Tyr
545                 550                 555                 560

Gly Gln Val Phe Ser Lys Leu Cys Pro Asp Asn Asp Lys Gln Val Met
                565                 570                 575

Leu Leu Ser Gln Val Ser Thr Tyr Trp Lys Asn Asn Val Gln Met Thr
            580                 585                 590

Ala Val Ala Ile Asp Arg Met Met Gly Tyr Arg Leu Val Ser Asn Gln
        595                 600                 605

Ala Ile Val Arg Trp Val Phe Ser Pro Glu Asn Val Asp Gln Phe His
    610                 615                 620

Val Ser Asp Gln Pro Trp Glu Ile Leu Gly Asn Ala Leu Asn Lys Thr
625                 630                 635                 640

Tyr Asn Arg Ile Ser Asp Leu Arg Lys Asp Ile Ser Asn Ile Thr Lys
                645                 650                 655

Asn Val Leu Val Ala Glu Lys Ala Ser Ala Asn Ala Arg Val Glu Leu
            660                 665                 670

Glu Ala Ala Glu Ser Lys Leu Ser Leu Val Glu Gly Glu Pro Val Leu
        675                 680                 685
```

```
Gly Glu Asn Pro Ala Lys Met Lys Arg Leu Lys Ser Thr Val Glu Lys
    690                 695                 700
Thr Gly Glu Ala Glu Leu Ser Leu Arg Glu Ser Leu Glu Ala Lys Glu
705                 710                 715                 720
Ala Leu Leu Asn Arg Ala Leu Ser Glu Thr Glu Val Leu Leu Leu Leu
                725                 730                 735
Leu Phe Gln Ser Phe Leu Gly Val Leu Lys Glu Arg Leu Pro Asp Pro
            740                 745                 750
Thr Lys Val Arg Ser Val Gln Asp Leu Lys Ser Ile Gly Ala Glu Asp
        755                 760                 765
Asp Lys Pro Ser Ala Met Asp Val Asp Ser Glu Asn Gly Asn Pro Lys
    770                 775                 780
Lys Ser Cys Glu Val Gly Glu Arg Glu Gln Trp Cys Leu Ser Thr Leu
785                 790                 795                 800
Gly Tyr Leu Thr Ala Phe Thr Arg Gln Tyr Ala Ser Glu Ile Trp Pro
                805                 810                 815
His Met Glu Lys Leu Glu Ser Glu Val Phe Ser Gly Glu Asp Val His
            820                 825                 830
Pro Leu Phe Leu Gln Ala Ile Ser Ser Ala Leu Gln Phe Pro Leu His
        835                 840                 845

<210> SEQ ID NO 19

<400> SEQUENCE: 19

000

<210> SEQ ID NO 20
<211> LENGTH: 7
<212> TYPE: PRT
<213> ORGANISM: Oryza sativa

<400> SEQUENCE: 20

Pro Pro Thr Ile Ser Gln Ser
1               5

<210> SEQ ID NO 21
<211> LENGTH: 27
<212> TYPE: PRT
<213> ORGANISM: Oryza sativa

<400> SEQUENCE: 21

His Ile Ala Met Leu Asp Gln Glu Ile Phe Val Gly Asn Ile His Pro
1               5                  10                  15
Leu Ile Arg Lys Ala Ala Phe Ser Gly Leu Cys
            20                  25

<210> SEQ ID NO 22
<211> LENGTH: 27
<212> TYPE: PRT
<213> ORGANISM: Zea mays

<400> SEQUENCE: 22

His Leu Gly His Cys His Leu Glu Val Leu Leu Gly Asn Val His Pro
1               5                  10                  15
Ser Leu Thr Lys Ser Lys His Ser Ser Leu Cys
            20                  25
```

<210> SEQ ID NO 23
<211> LENGTH: 75
<212> TYPE: PRT
<213> ORGANISM: Oryza sativa

<400> SEQUENCE: 23

```
Leu Leu Phe Phe Asn Gly Cys Arg Lys Glu Cys Ala Phe Tyr Leu Val
1               5                   10                  15

Ser Leu Pro Val Pro Phe Arg Tyr Glu Tyr Leu Met Ala Glu Thr Ile
            20                  25                  30

Phe Ser Gln Leu Leu Leu Pro Asn Pro Pro Phe Arg Pro Ile Tyr
        35                  40                  45

Tyr Thr Leu Val Ile Ile Asp Leu Cys Lys Ala Leu Pro Gly Ala Phe
    50                  55                  60

Pro Ser Val Val Val Gly Ala Val His Ala Leu
65                  70                  75
```

<210> SEQ ID NO 24
<211> LENGTH: 78
<212> TYPE: PRT
<213> ORGANISM: Zea mays
<220> FEATURE:
<221> NAME/KEY: SITE
<222> LOCATION: (1)...(78)
<223> OTHER INFORMATION: Xaa = Any Amino Acid

<400> SEQUENCE: 24

```
Leu Leu Leu Phe Ser Phe Ile His Thr Ser Cys Xaa Arg Phe Leu Val
1               5                   10                  15

Pro Phe Phe Ser Leu Phe Leu Val Ser Leu Ser Leu Phe Ser Leu Leu
            20                  25                  30

Phe Leu Leu Pro Cys Pro Val Phe Ser Leu Met Leu Phe Leu Tyr Leu
        35                  40                  45

Phe Leu Leu Ser Asn Val Pro Asp Leu Glu Ala Ala Pro Arg Ala Phe
    50                  55                  60

His Pro Pro Pro His Phe Leu Ile Xaa Phe Thr His Pro Ile
65                  70                  75
```

<210> SEQ ID NO 25
<211> LENGTH: 206
<212> TYPE: PRT
<213> ORGANISM: Oryza sativa

<400> SEQUENCE: 25

```
Ser Gln Ser Ser Glu Ile Val Lys Gly Gln Glu Lys His Glu Ala
1               5                   10                  15

Asp Leu Lys Tyr Pro Gln Arg Leu Arg Arg Leu His Ile Phe Pro Thr
            20                  25                  30

Asn Lys Ala Glu Asn Met Gln Pro Val Asp Arg Phe Val Val Glu Glu
        35                  40                  45

Cys Ile Leu Asp Val Leu Leu Phe Phe Asn Gly Cys Arg Lys Glu Cys
    50                  55                  60

Ala Phe Tyr Leu Val Ser Leu Pro Val Pro Phe Arg Tyr Glu Tyr Leu
65                  70                  75                  80

Met Ala Glu Thr Ile Phe Ser Gln Leu Leu Leu Leu Pro Asn Pro Pro
            85                  90                  95

Phe Arg Pro Ile Tyr Tyr Thr Leu Val Ile Ile Asp Leu Cys Lys Ala
        100                 105                 110
```

```
Leu Pro Gly Ala Phe Pro Ser Val Val Gly Ala Val His Ala Leu
        115                 120                 125

Phe Asp Arg Ile Ser Asn Met Asp Met Glu Cys Arg Thr Arg Leu Ile
130                 135                 140

Leu Trp Phe Ser His His Leu Ser Asn Phe Gln Phe Ile Trp Pro Trp
145                 150                 155                 160

Gln Glu Trp Ala Tyr Val Lys Asp Leu Pro Lys Trp Ala Pro Gln Arg
                165                 170                 175

Val Phe Val Gln Glu Val Leu Glu Arg Glu Ile Arg Leu Ser Tyr Phe
            180                 185                 190

Asp Lys Ile Lys Gln Ser Ile Glu Asp Ala Val Glu Leu Glu
        195                 200                 205

<210> SEQ ID NO 26
<211> LENGTH: 206
<212> TYPE: PRT
<213> ORGANISM: Triticum aestivum

<400> SEQUENCE: 26

Thr Met Ser Ser Ser Glu Ile Leu Lys Gly Gln Glu Met His Glu Ala
1               5                   10                  15

Asn Leu Lys Tyr Pro Gln Arg Leu Arg Arg Leu His Ile Phe Pro Thr
            20                  25                  30

Asn Lys Ala Glu Asn Met Gln Pro Val Asp Arg Phe Val Val Glu Glu
        35                  40                  45

Tyr Ile Leu Asp Val Leu Leu Phe Phe Asn Gly Cys Arg Lys Glu Cys
    50                  55                  60

Ala Phe Tyr Leu Val Ser Leu Pro Val Ser Phe Arg Tyr Glu Tyr Leu
65                  70                  75                  80

Met Ala Glu Thr Ile Phe Ser Gln Leu Leu Leu Pro Asn Pro Pro
                85                  90                  95

Phe Arg Pro Ile Tyr Tyr Thr Leu Val Ile Ile Asp Leu Cys Lys Ala
                100                 105                 110

Leu Pro Ala Ala Phe Pro Ser Val Val Ala Ala Val His Ala Leu
        115                 120                 125

Phe Asp Arg Ile Ser Asn Met Asp Thr Glu Cys Arg Thr Arg Leu Ile
130                 135                 140

Leu Trp Phe Ser His His Leu Ser Asn Phe Gln Phe Ile Trp Pro Trp
145                 150                 155                 160

Gln Glu Trp Ala Asn Val Lys Gly Leu Pro Lys Trp Ala Pro Gln Arg
                165                 170                 175

Val Phe Val Gln Glu Val Leu Glu Arg Glu Ile Arg Leu Ser Tyr Phe
            180                 185                 190

Glu Lys Ile Lys Gln Ser Ile Glu Asp Ala Ala Glu Leu Glu
        195                 200                 205

<210> SEQ ID NO 27
<211> LENGTH: 217
<212> TYPE: PRT
<213> ORGANISM: Oryza sativa

<400> SEQUENCE: 27

Lys Glu Ile Gln Thr Leu Arg Lys Gly Leu Gln Ala Ala Lys Glu Ala
1               5                   10                  15

Ser Glu Lys Ala Ala Arg Glu Leu Glu Glu Ala Lys Ser Ile Ile Glu
            20                  25                  30
```

Ile Val Asp Gly Gln Pro Val Pro Ser Glu Asn Pro Gly Arg Leu Arg
        35                  40                  45

Arg Leu Gln Ala Arg Ala Asp Lys Ala Lys Glu Gly Glu Val Thr Thr
 50                  55                  60

Glu Glu Ser Leu Glu Ala Lys Glu Ala Leu Leu Ala Arg Gly Leu Glu
 65                  70                  75                  80

Glu Ser Lys Glu Leu Leu Arg Leu Leu Phe Lys Ser Phe Val Glu Val
                 85                  90                  95

Leu Thr Glu Arg Leu Pro Pro Ile Ser Ala Asp Gly Asp Val Pro Asn
            100                 105                 110

Leu Arg Ala Gly Asp Pro Asn Val Asn Ser Ser Ala Arg Asp Pro Glu
        115                 120                 125

Ala Thr Thr Met Glu Ile Asp Asn Glu Asn Gly Gly Asp Asn Asp Ser
    130                 135                 140

Ser Gln Leu Asn Gly Gln Asn Lys Lys Ile Ser His Asn Val Gly Glu
145                 150                 155                 160

Leu Glu Gln Trp Cys Leu Cys Thr Leu Gly Tyr Leu Lys Ser Phe Ser
                165                 170                 175

Arg Gln Tyr Ala Thr Glu Ile Trp Ser His Ile Ala Met Leu Asp Gln
            180                 185                 190

Glu Ile Phe Val Gly Asn Ile His Pro Leu Ile Arg Lys Ala Ala Phe
        195                 200                 205

Ser Gly Leu Cys Arg Pro Thr Ser Glu
    210                 215

<210> SEQ ID NO 28
<211> LENGTH: 216
<212> TYPE: PRT
<213> ORGANISM: Triticum aestivum

<400> SEQUENCE: 28

Arg Lys Phe Arg Gln Leu Arg Lys Ser Ile Gln Val Ala Lys Glu Ala
 1               5                  10                  15

Ser Ala Lys Ala Ile Lys Glu Leu Glu Glu Ala Lys Ser Ile Leu Glu
             20                  25                  30

Ile Val Glu Gly Gln Pro Val Pro Ser Glu Arg Pro Gly Arg Leu Arg
        35                  40                  45

Arg Leu Gln Gly Phe Ala Asp Lys Ala Lys Glu Glu Glu Val Thr Ile
 50                  55                  60

Glu Glu Ser Leu Glu Ala Lys Gln Ala Leu Leu Ala Leu Gly Leu Glu
 65                  70                  75                  80

Glu Gly Lys Glu Leu Leu Arg Leu Leu Phe Lys Ser Phe Leu Asp Val
                 85                  90                  95

Leu Thr Glu Arg Leu Pro Pro Val Ser Ala Asp Gly Asp Val Pro Asn
            100                 105                 110

Leu Arg Ala Gly Asp Pro Asn Val Thr Phe Pro Ala Ser Asp Pro Glu
        115                 120                 125

Ala Ala Thr Met Glu Ile Asp Asn Glu Asn Gly Ala Asp Asn Asn Ser
    130                 135                 140

Gln Val Asn Arg Glu Asn Thr Glu Ala Gly Tyr Thr Ile Gly Glu Leu
145                 150                 155                 160

Glu Gln Trp Cys Leu Cys Thr Leu Gly Tyr Leu Lys Ser Phe Ser Arg
                165                 170                 175

Gln Tyr Ala Thr Glu Ile Trp Ser His Ile Gly Met Leu Asp Asp Glu
            180                 185                 190

```
Val Phe Val Gly Ser Ile His Pro Leu Ile Arg Lys Ala Ala Phe Ser
            195                 200                 205

Gly Leu Cys Arg Gln Met Asn Gln
    210                 215

<210> SEQ ID NO 29
<211> LENGTH: 186
<212> TYPE: PRT
<213> ORGANISM: Oryza sativa

<400> SEQUENCE: 29

Glu Ile Val Asp Gly Gln Pro Val Pro Ser Glu Asn Pro Gly Arg Leu
 1               5                  10                  15

Arg Arg Leu Gln Ala Arg Ala Asp Lys Ala Lys Glu Gly Glu Val Thr
            20                  25                  30

Thr Glu Glu Ser Leu Glu Ala Lys Glu Ala Leu Leu Ala Arg Gly Leu
        35                  40                  45

Glu Glu Ser Lys Glu Leu Leu Arg Leu Leu Phe Lys Ser Phe Val Glu
    50                  55                  60

Val Leu Thr Glu Arg Leu Pro Pro Ile Ser Ala Asp Gly Asp Val Pro
65                  70                  75                  80

Asn Leu Arg Ala Gly Asp Pro Asn Val Asn Ser Ser Ala Arg Asp Pro
                85                  90                  95

Glu Ala Thr Thr Met Glu Ile Asp Asn Glu Asn Gly Gly Asp Asn Asp
            100                 105                 110

Ser Ser Gln Leu Asn Gly Gln Asn Lys Lys Ile Ser His Asn Val Gly
        115                 120                 125

Glu Leu Glu Gln Trp Cys Leu Cys Thr Leu Gly Tyr Leu Lys Ser Phe
    130                 135                 140

Ser Arg Gln Tyr Ala Thr Glu Ile Trp Ser His Ile Ala Met Leu Asp
145                 150                 155                 160

Gln Glu Ile Phe Val Gly Asn Ile His Pro Leu Ile Arg Lys Ala Ala
                165                 170                 175

Phe Ser Gly Leu Cys Arg Pro Thr Ser Glu
            180                 185

<210> SEQ ID NO 30
<211> LENGTH: 185
<212> TYPE: PRT
<213> ORGANISM: Triticum aestivum

<400> SEQUENCE: 30

Glu Ile Val Gly Ala Gln Pro Val Ser Ser Glu Arg Pro Gly Arg Leu
 1               5                  10                  15

Arg Arg Leu Gln Gly Phe Ala Asp Lys Ala Lys Glu Glu Glu Val Thr
            20                  25                  30

Ile Glu Glu Ser Leu Glu Ala Lys Gln Ala Leu Leu Ala Arg Gly Leu
        35                  40                  45

Glu Glu Gly Lys Glu Leu Leu Arg Leu Leu Phe Lys Ser Phe Val Asp
    50                  55                  60

Val Leu Thr Glu Cys Leu Pro Pro Val Ser Ala Asp Gly Asp Val Pro
65                  70                  75                  80

Asn Leu Arg Ala Gly Asp Pro Asn Val Thr Phe Pro Ala Ser Asp Pro
                85                  90                  95

Glu Ala Val Thr Met Glu Ile Asp Asn Glu Asn Gly Ala Asp Asn Asn
            100                 105                 110
```

```
Ser Gln Val Asn Gly Glu Asn Thr Glu Val Gly Tyr Thr Ile Gly Glu
        115                 120                 125

Leu Glu Gln Trp Cys Leu Cys Thr Leu Gly Tyr Leu Lys Ser Phe Ser
        130                 135                 140

Arg Gln Tyr Ala Thr Glu Ile Trp Ser His Ile Gly Met Leu Asp Glu
145                 150                 155                 160

Glu Val Phe Val Glu Ser Ile His Pro Leu Ile Arg Lys Ala Ala Phe
                165                 170                 175

Ser Gly Leu Cys Arg Gln Met Asn Gln
        180                 185

<210> SEQ ID NO 31
<211> LENGTH: 189
<212> TYPE: PRT
<213> ORGANISM: Oryza sativa

<400> SEQUENCE: 31

Ser Ile Ile Glu Ile Val Asp Gly Gln Pro Val Pro Ser Glu Asn Pro
1               5                   10                  15

Gly Arg Leu Arg Arg Leu Gln Ala Arg Ala Asp Lys Ala Lys Glu Gly
            20                  25                  30

Glu Val Thr Thr Glu Glu Ser Leu Glu Ala Lys Glu Ala Leu Leu Ala
        35                  40                  45

Arg Gly Leu Glu Glu Ser Lys Glu Leu Leu Arg Leu Leu Phe Lys Ser
    50                  55                  60

Phe Val Glu Val Leu Thr Glu Arg Leu Pro Pro Ile Ser Ala Asp Gly
65                  70                  75                  80

Asp Val Pro Asn Leu Arg Ala Gly Asp Pro Asn Val Asn Ser Ser Ala
                85                  90                  95

Arg Asp Pro Glu Ala Thr Thr Met Glu Ile Asp Asn Glu Asn Gly Gly
            100                 105                 110

Asp Asn Asp Ser Ser Gln Leu Asn Gly Gln Asn Lys Lys Ile Ser His
        115                 120                 125

Asn Val Gly Glu Leu Glu Gln Trp Cys Leu Cys Thr Leu Gly Tyr Leu
    130                 135                 140

Lys Ser Phe Ser Arg Gln Tyr Ala Thr Glu Ile Trp Ser His Ile Ala
145                 150                 155                 160

Met Leu Asp Gln Glu Ile Phe Val Gly Asn Ile His Pro Leu Ile Arg
                165                 170                 175

Lys Ala Ala Phe Ser Gly Leu Cys Arg Pro Thr Ser Glu
            180                 185

<210> SEQ ID NO 32
<211> LENGTH: 187
<212> TYPE: PRT
<213> ORGANISM: Triticum aestivum

<400> SEQUENCE: 32

Ser Ile Leu Glu Ile Val Glu Gly Pro Thr Cys Val Ile Lys Thr Arg
1               5                   10                  15

Ala Gly Asp Asp Phe Lys Ala Leu Leu Thr Lys Gln Lys Lys Glu Glu
            20                  25                  30

Val Thr Ile Glu Glu Ser Leu Glu Ala Lys Gln Ala Leu Leu Ala Arg
        35                  40                  45

Gly Leu Glu Glu Gly Lys Glu Leu Leu Arg Leu Leu Phe Lys Ser Phe
    50                  55                  60
```

```
Val Asp Val Leu Thr Glu Arg Leu Pro Val Ser Ala Asp Gly Asp
 65                  70                  75                  80

Val Pro Asn Leu Arg Ala Gly Asp Pro Asn Val Thr Phe Pro Ala Ser
                 85                  90                  95

Asp Pro Glu Ala Ala Thr Met Glu Ile Asp Asp Glu Asn Gly Ala Asp
            100                 105                 110

Asn Asn Ser Gln Val Asn Gly Glu Asn Met Lys Ala Gly Tyr Thr Ile
            115                 120                 125

Gly Glu Leu Glu Gln Trp Cys Leu Cys Thr Leu Gly Tyr Leu Lys Ser
130                 135                 140

Phe Ser Arg Gln Tyr Ala Thr Glu Ile Trp Ser His Ile Gly Met Leu
145                 150                 155                 160

Asp Glu Glu Val Phe Val Gly Ser Ile His Pro Leu Ile Arg Lys Ala
                165                 170                 175

Ala Phe Ser Gly Leu Cys Arg Gln Met Asn Gln
                180                 185

<210> SEQ ID NO 33
<211> LENGTH: 94
<212> TYPE: PRT
<213> ORGANISM: Oryza sativa

<400> SEQUENCE: 33

Ala Ser Leu Pro Trp Gly Gly Ser Glu Leu Phe Glu Gln Val Pro Asp
  1               5                  10                  15

Glu Phe Glu Arg Val Leu Val Gly Ile Gln Ser Tyr Ile Ser Ile Arg
                 20                  25                  30

Arg His Phe Asp Asp Ile Ala Phe Ser Val Phe Glu Thr Asp Glu Gly
             35                  40                  45

Asn Ser Pro Asn Lys Lys Asp Phe Ile Glu Asp Leu Trp Glu Arg Ile
         50                  55                  60

Gln Val Leu Ser Arg Asn Gly Trp Lys Val Lys Ser Val Pro Lys Pro
 65                  70                  75                  80

His Leu Ser Phe Glu Ala Gln Leu Val Ala Gly Val Ser His
                 85                  90

<210> SEQ ID NO 34
<211> LENGTH: 94
<212> TYPE: PRT
<213> ORGANISM: Triticum aestivum

<400> SEQUENCE: 34

Ala Ser Leu Pro Trp Gly Gly Ser Glu Leu Phe Glu Gln Ala Pro Asp
  1               5                  10                  15

Glu Leu Glu Arg Val Leu Val Gly Ile Gln Ser Tyr Ile Ser Ile Arg
                 20                  25                  30

Arg His Phe Asp Asp Ile Ala Phe Ser Val Phe Glu Thr Asp Glu Gly
             35                  40                  45

Asn Ser Pro Asn Lys Lys Asp Phe Met Glu Asp Leu Trp Glu Arg Met
         50                  55                  60

Gln Leu Leu Ser Arg Asn Gly Trp Lys Val Lys Ser Val Pro Lys Pro
 65                  70                  75                  80

His Leu Ser Phe Glu Ala Gln Leu Val Val Gly Lys Ser His
                 85                  90
```

```
<210> SEQ ID NO 35
<211> LENGTH: 88
<212> TYPE: PRT
<213> ORGANISM: Oryza sativa

<400> SEQUENCE: 35

Glu Thr Asp Glu Gly Asn Ser Pro Asn Lys Lys Asp Phe Ile Glu Asp
1               5                   10                  15

Leu Trp Glu Arg Ile Gln Val Leu Ser Arg Asn Gly Trp Lys Val Lys
            20                  25                  30

Ser Val Pro Lys Pro His Leu Ser Phe Glu Ala Gln Leu Val Ala Gly
        35                  40                  45

Val Ser His Arg Phe Ser Pro Ile Ser Cys Pro Pro Thr Ile Ser
    50                  55                  60

Gln Ser Ser Glu Ile Val Lys Gly Gln Lys His Glu Ala Asp
65                  70                  75                  80

Leu Lys Tyr Pro Gln Arg Leu Arg
                85

<210> SEQ ID NO 36
<211> LENGTH: 75
<212> TYPE: PRT
<213> ORGANISM: Triticum aestivum

<400> SEQUENCE: 36

Glu Gly Asp Glu Gly Glu Asp Asp Ser Asp Ser Gly Ser Asp
1               5                   10                  15

Glu Gln His Arg Gly Lys Asn Gly Trp Glu Ala Pro Ala Leu Pro Pro
            20                  25                  30

Pro Arg Leu Ser Val Asn Thr Gln Thr Gly Ala Ser Ala Ala Arg Arg
        35                  40                  45

Gly Gly Ser Phe Arg Ser Pro Arg Ser Tyr Ser Leu Ser Asp Leu Arg
    50                  55                  60

Asn Gly Gly Asp Ala Ser Tyr Asn Gln Leu Arg
65                  70                  75

<210> SEQ ID NO 37
<211> LENGTH: 88
<212> TYPE: PRT
<213> ORGANISM: Oryza sativa

<400> SEQUENCE: 37

Glu Thr Asp Glu Gly Asn Ser Pro Asn Lys Lys Asp Phe Ile Glu Asp
1               5                   10                  15

Leu Trp Glu Arg Ile Gln Val Leu Ser Arg Asn Gly Trp Lys Val Lys
            20                  25                  30

Ser Val Pro Lys Pro His Leu Ser Phe Glu Ala Gln Leu Val Ala Gly
        35                  40                  45

Val Ser His Arg Phe Ser Pro Ile Ser Cys Pro Pro Thr Ile Ser
    50                  55                  60

Gln Ser Ser Glu Ile Val Lys Gly Gln Lys His Glu Ala Asp
65                  70                  75                  80

Leu Lys Tyr Pro Gln Arg Leu Arg
                85

<210> SEQ ID NO 38
<211> LENGTH: 75
<212> TYPE: PRT
<213> ORGANISM: Triticum aestivum
```

-continued

```
<400> SEQUENCE: 38

Glu Gly Glu Glu Gly Glu Asp Asp Asp Ser Asp Ser Gly Ser Asp
1               5                   10                  15

Glu Gln His Arg Gly Lys Asn Gly Trp Glu Ala Pro Ala Leu Pro Pro
            20                  25                  30

Pro Arg Leu Ser Val Asn Thr Gln Met Gly Ala Ala Ala Arg Lys
        35                  40                  45

Gly Gly Ser Phe Arg Ser Pro Arg Ser Tyr Ser Leu Ser Asp Leu Arg
    50                  55                  60

Asn Gly Gly Asp Ala Arg Tyr Asn Gln Leu Arg
65                  70                  75

<210> SEQ ID NO 39
<211> LENGTH: 39
<212> TYPE: PRT
<213> ORGANISM: Oryza sativa

<400> SEQUENCE: 39

Gly Asp Pro Asn Val Asn Ser Ser Ala Arg Asp Pro Glu Ala Thr Thr
1               5                   10                  15

Met Glu Ile Asp Asn Glu Asn Gly Gly Asp Asn Asp Ser Ser Gln Leu
            20                  25                  30

Asn Gly Gln Asn Lys Lys Ile
        35

<210> SEQ ID NO 40
<211> LENGTH: 39
<212> TYPE: PRT
<213> ORGANISM: Triticum aestivum

<400> SEQUENCE: 40

Gly Asp Pro Thr Pro Gly Gln Glu Pro Gln Pro Arg Arg Lys Glu
1               5                   10                  15

Ala Ala Pro Ser Gly Asp Asn Gly Gly Asp Ser Asp Gly Gly Asp Leu
            20                  25                  30

Gly Gly Glu Glu Ser Arg Val
        35

<210> SEQ ID NO 41
<211> LENGTH: 63
<212> TYPE: PRT
<213> ORGANISM: Oryza sativa

<400> SEQUENCE: 41

Arg Asn Gly Trp Lys Val Lys Ser Val Pro Lys Pro His Leu Ser Phe
1               5                   10                  15

Glu Ala Gln Leu Val Ala Gly Val Ser His Arg Phe Ser Pro Ile Ser
            20                  25                  30

Cys Pro Pro Pro Thr Ile Ser Gln Ser Ser Ser Glu Ile Val Lys Gly
        35                  40                  45

Gln Glu Lys His Glu Ala Asp Leu Lys Tyr Pro Gln Arg Leu Arg
    50                  55                  60

<210> SEQ ID NO 42
<211> LENGTH: 54
<212> TYPE: PRT
<213> ORGANISM: Triticum aestivum
```

```
<400> SEQUENCE: 42

Lys Asn Gly Trp Glu Ala Pro Ala Leu Pro Pro Arg Leu Ser Val
1               5                  10                 15

Asn Thr Gln Met Gly Ala Ser Ala Ala Arg Arg Gly Gly Ser Phe Arg
                20                  25                  30

Ser Pro Arg Ser Tyr Ser Leu Ser Asp Leu Arg Asn Gly Gly Asp Ala
            35                  40                  45

Ser Tyr Asn Gln Leu Arg
        50

<210> SEQ ID NO 43
<211> LENGTH: 102
<212> TYPE: PRT
<213> ORGANISM: Oryza sativa

<400> SEQUENCE: 43

Val Asn Ser Ser Ala Arg Asp Pro Glu Ala Thr Thr Met Glu Ile Asp
1               5                  10                  15

Asn Glu Asn Gly Gly Asp Asn Asp Ser Ser Gln Leu Asn Gly Gln Asn
                20                  25                  30

Lys Lys Ile Ser His Asn Val Gly Glu Leu Glu Gln Trp Cys Leu Cys
            35                  40                  45

Thr Leu Gly Tyr Leu Lys Ser Phe Ser Arg Gln Tyr Ala Thr Glu Ile
        50                  55                  60

Trp Ser His Ile Ala Met Leu Asp Gln Glu Ile Phe Val Gly Asn Ile
65                  70                  75                  80

His Pro Leu Ile Arg Lys Ala Ala Phe Ser Gly Leu Cys Arg Pro Thr
                85                  90                  95

Ser Glu Gly Ser His Leu
            100

<210> SEQ ID NO 44
<211> LENGTH: 99
<212> TYPE: PRT
<213> ORGANISM: Musa acuminata
<220> FEATURE:
<221> NAME/KEY: SITE
<222> LOCATION: (1)...(99)
<223> OTHER INFORMATION: Xaa = Any Amino Acid

<400> SEQUENCE: 44

Ile Asp Ser Met Ala Ile Asp Leu Glu Glu Ser Ser Thr Met Glu Met
1               5                  10                  15

Asp His Asp Asn Arg Arg Lys Asp Asp Arg Asn Gly Glu Lys Val Thr
                20                  25                  30

His Arg Tyr Ser Leu Lys Glu Gln Asp Gln Trp Cys Leu Cys Thr Leu
            35                  40                  45

Gly Tyr Val Lys Ala Phe Ser Arg Gln Tyr Xaa Thr Glu Val Trp Pro
        50                  55                  60

His Leu Glu Thr Leu Glu Ala Glu Val Phe Gly Gly Asp Ile His Pro
65                  70                  75                  80

Leu Phe Arg Lys Ala Val Phe Ser Gly Leu Cys Arg Ser Thr Thr Glu
                85                  90                  95

Met His Leu
```

<210> SEQ ID NO 45
<211> LENGTH: 59
<212> TYPE: PRT
<213> ORGANISM: Oryza sativa

<400> SEQUENCE: 45

Trp Gln Glu Trp Ala Tyr Val Lys Asp Leu Pro Lys Trp Ala Pro Gln
1               5                   10                  15

Arg Val Phe Val Gln Glu Val Leu Glu Arg Glu Ile Arg Leu Ser Tyr
            20                  25                  30

Phe Asp Lys Ile Lys Gln Ser Ile Glu Asp Ala Val Glu Leu Glu Glu
        35                  40                  45

Leu Leu Pro Pro Lys Ala Gly Pro Asn Phe Arg
    50                  55

<210> SEQ ID NO 46
<211> LENGTH: 69
<212> TYPE: PRT
<213> ORGANISM: Musa acuminata

<400> SEQUENCE: 46

Trp Asn Lys Trp Glu Asn Trp Lys Asp Leu Arg Lys Trp Glu Pro Arg
1               5                   10                  15

Arg Ile Gly Ala Leu Ile Leu Tyr Ile Ile Val Val Ser Ile Ser Ser
            20                  25                  30

Arg Lys Phe Tyr Val Ala Leu Thr Ser Gln Ile Asn Arg Gln Ser Lys
        35                  40                  45

Arg Glu Leu Thr Glu Ala Tyr Met Glu Ala Leu Ile Pro Glu Pro Ser
    50                  55                  60

Pro Ala Asn Leu Arg
65

<210> SEQ ID NO 47
<211> LENGTH: 55
<212> TYPE: PRT
<213> ORGANISM: Oryza sativa

<400> SEQUENCE: 47

Pro Val Asp Arg Phe Val Val Glu Glu Cys Ile Leu Asp Val Leu Leu
1               5                   10                  15

Phe Phe Asn Gly Cys Arg Lys Glu Cys Ala Phe Tyr Leu Val Ser Leu
            20                  25                  30

Pro Val Pro Phe Arg Tyr Glu Tyr Leu Met Ala Glu Thr Ile Phe Ser
        35                  40                  45

Gln Leu Leu Leu Pro Asn
    50              55

<210> SEQ ID NO 48
<211> LENGTH: 53
<212> TYPE: PRT
<213> ORGANISM: Musa acuminata

<400> SEQUENCE: 48

Pro Ala Ile Ile Phe Ile Val Ser Glu Ile Val Asp Leu Leu Phe
1               5                   10                  15

Gly Val Gly Cys Gln Gln Ser Ser Phe Ser Ile Leu Ser Gly Pro Pro
            20                  25                  30

```
Phe Arg Cys Tyr Val His Leu Ile Gly Ser Val Ile Val Ser Arg Cys
         35                  40                  45

Val Phe Arg Pro Ser
     50

<210> SEQ ID NO 49
<211> LENGTH: 283
<212> TYPE: DNA
<213> ORGANISM: Triticum aestivum

<400> SEQUENCE: 49
gtgagatttt ccaactacta actgagcttc aaacgacaag tgaggttttg aacactttt      60 aaccttccac ccattacgag aaagaagttg catacgctcc catagatctt ccatgaaatc    120
cttcttattg ggagagttgc cttcgtccgt ctcgaagact gagaaagcaa tatcatcaaa    180
atgccttctg atgcttatat aagactgtat accaaccaga accctctcga gttcatccgg    240
ggcttgctcg aacaattctg aaccacccca tggaagggaa gcc                      283

<210> SEQ ID NO 50
<211> LENGTH: 799
<212> TYPE: DNA
<213> ORGANISM: Triticum aestivum

<400> SEQUENCE: 50
cagtgatctt cggaaggaaa ttcagacaac tgaggaaaag tattcaagtt gctaaagagg     60
ctagtgcaaa agccatcaaa gagttggagg aggctaaatc aatacttgaa atcgtagagg    120
gccaacctgt gccatctgaa agaccaggca ggctgagacg cttcaaggt tttgctgaca     180 aagcaaaaga agaggaagta actattgaag aatcgttaga ggcaaagcag gctctccttg    240
ccctggggct tgaagaaggc aaagaattgc ttaggttatt attcaagagc tttcttgatg    300
tgcttactga acgcctgcca cctgtttctg ctgatggaga tgttcctaac ctacgcgctg    360
gagatcctaa tgtaacattt ccagccagtg atcctgaagc ggcaactatg agatagaca    420 atgaaaatgg agcagataac aatagtcaag tgaatcgtga aaatacggaa gctggttata    480
ctattggaga gcttgagcaa tggtgcctat gcacattggg gtatctaaag tcattttctc    540
gacagtatgc aacagagatt tggtctcaca ttggcatgtt ggacgatgag gtttttgttg    600
ggagtattca ccctctcatc cggaaagccg cattctccgg tttgtgcaga cagatgaacc    660
agtgaagggt tgtaactcag ctttgattcc tgaccatcct ggtcttgaaa acgacctgta    720
aagacaagct gtaacaacat tcttgactaa ttctgacatg tgggcaacat catcgcaccc    780
aagaattccc tgtttggta                                                 799

<210> SEQ ID NO 51
<211> LENGTH: 771
<212> TYPE: DNA
<213> ORGANISM: Triticum aestivum

<400> SEQUENCE: 51
caaagccatc aaagaattgg aggagcctaa tcaagacgtg aaatcgtaga ggcccaacct     60
gtgtcatctg aaagaccagg caggctgaga cgacttcaag gttttgctga caaagcaaaa    120
gaagaggaag taactattga agaatcgtta gaggcaaagc aggctctcct tgcccgggg     180 cttgaagaag gcaaagaatt gcttaggtta ttattcaaga gctttgttga tgtgcttact    240
gaatgcctgc cacctgtttc tgctgatgga gatgttccta acctacgcgc tggagatcct    300
aatgtaacat ttccagccag cgatcctgaa gcggtaacta tggagataga caatgaaaat    360
```

```
ggagcagata acaatagtca agtgaatggt gaaaatacgg aagttggtta tactattgga      420
gagcttgagc aatggtgctt atgcacattg gggtatctaa agtcattttc tcgacagtat      480
gcaacagaga tttggtctca cattggcatg ttggacgagg aggttttcgt tgagagtatt      540
caccctctta ttcgaaaagc cgcattctcc ggtttgtgca gacagatgaa ccagtgaagg      600
gttgtaactc agctttgatt cctgaccatc atggttttga aaacgacctg taaagacaag      660
ctgtaacaac attcttgact aattctgaca tgtcggcaac actcgcatcc aagaattccc      720
tgtttggtag ttatgttggt cagtttacgt ggggcgcatt ttcatttgtc c              771

<210> SEQ ID NO 52
<211> LENGTH: 846
<212> TYPE: DNA
<213> ORGANISM: Triticum aestivum

<400> SEQUENCE: 52
gagaaggcta aatcaatact tgaaatcgta gagggcccaa cctgtgtcat ctgaaagacc       60
agggcaggct gagacgactt caaggctttg ctgacaaagc aaaagaaaga ggaagtaact      120
attgaagaat cgttagaggc aaagcaggct ctccttgccc gggccttga agaaggcaaa       180 gaattgctta ggttattatt caagagcttt gttgatgtgc ttactgaacg cctgccacct      240
gtttctgctg atggagatgt tcctaaccta cgcgctggag atcctaatgt aacatttcca      300
gccagcgatc ctgaagcggc aactatggag atagacgatg aaaatggagc agataacaat      360
agtcaagtga atggtgaaaa tatgaaagct ggttatacta ttggagagct tgagcaatgg      420
tgcctgtgca cattggggta tctaaagtca ttttctcgac agtatgcaac agagatttgg      480
tctcacattg gcatgttgga cgaggaggtt tttgttggga gtattcaccc tctcatccgg      540
aaagccgcat tctccggttt gtgcagacag atgaaccagt gaagggttgt aactcagctt      600
tgattcctga ccatcatggt cttgaaaacg acctgtaaag acaagctgta acaacattct      660
tgagtaattc tgacatgtcg gcaacaacac tcgcacccaa gaattccctg tttgatagtt      720
atgttggcca gtacgtggg agctatgcat tttcatttgt ctatggtgac agtttgggtg      780
gagtaatctt gacgtgtatt tagctttttt gcacactctg cttgagactt gaaaaggtgt      840
ttgata                                                                846

<210> SEQ ID NO 53
<211> LENGTH: 627
<212> TYPE: DNA
<213> ORGANISM: Triticum aestivum

<400> SEQUENCE: 53
tttcacgatg tcgtcttctg agatattaaa agggcaagag atgcatgaag ccaatctaaa       60
gtatcctcaa aggcttcgta ggctccatat atttccaaca aataaagctg agaatatgca      120
acctgtagac cgttttgttg ttgaggaata catattggat gtgctgcttt tcttcaatgg      180
atgtcgcaaa gaatgtgcgt tttatctggt cagccttcct gtgtcttttc ggtatgaata      240
cctgatggct gagaccatat tttcacagct actattgctg ccgaatccac ctttcaggcc      300
aatctactat acgttggtta tcatcgatct ttgcaaggct ttgccagctg catttccatc      360
tgtggtggta gcagcagtac atgctctttt tgatagaata agtaacatgg atacagagtg      420
ccgcaccaga cttatcctat ggttttcaca tcatttgtca aattttcaat tcatttggcc      480
ttggcaggag tgggccaatg tgaagggcct accaaaatgg gctccacaac gtgttttgt      540
```

-continued

```
ccaagaagta ctagaaaggg aaattcggtt gtcctatttc gagaaaatca agcagagtat      600
tgaagatgct gctgagttgg aagggtt                                         627

<210> SEQ ID NO 54
<211> LENGTH: 454
<212> TYPE: DNA
<213> ORGANISM: Musa acuminata
<220> FEATURE:
<221> NAME/KEY: misc_feature
<222> LOCATION: (1)...(454)
<223> OTHER INFORMATION: n = A,T,C or G

<400> SEQUENCE: 54
aattcttttc aatacagaac tttggttaca agactgaaat taagatggaa taaatagtat       60
acatccagaa gaggnnnnnn nnnnnnnnnn nnnnnnncta ttaagtgagg aatcaactaa      120
acaaagaaat gaaaaatcaa agatgtcaca tttctgtggt tgatcggcat aaaccagaaa      180
agacagcttt cctgaaaagc ggatggatat ctccaccaaa cacctcagct tccagtgttt      240
caagatgtgg ccaaacctct gttnnatact gccttgaaaa tgctttgacg taacccaatg      300
tgcataggca ccactggtct tgttctttaa gactgtagcg atgagttacc ttttcaccat      360
tcctatcatc ctttctcctg ttatcatggt ccatctccat ggtagatgac tcctccaaat      420
caatcgccat ggaatctata atcttcctca tccc                                 454
```

NUCLEIC ACIDS ENCODING ORYZA SATIVA NUCLEAR CAP BINDING PROTEIN 80 AND METHODS OF USE

This is a national stage application under 35 U.S.C. § 371 of International Application No. PCT/EP02/03809, filed Apr. 5, 2002, which is entitled to the benefit of United States Patent Application No. 60/282,370, filed Apr. 6, 2001, both of which are incorporated herein by reference in their entireties.

FIELD OF THE INVENTION

The present invention generally relates to the field of plant molecular biology, and more specifically to monocot nuclear cap binding protein 80 (CBP80) genes.

BACKGROUND OF THE INVENTION

Unpredictable rainfall, increases in soil salinity, and low temperature at the beginning or end of the growing season often result in decreased plant growth and crop productivity. These three environmental factors share at least one element of stress, and that is water deficit or dehydration.

Drought is a significant problem in agriculture today. Over the last 40 years, for example, drought accounted for 74% of the total U.S. crop losses of corn (U.S. Department of Agriculture, 1990. Agricultural Statistics. U.S. Government Printing Office, Washington, D.C.). To sustain productivity under adverse environmental conditions, it is important to provide crops with a genetic basis for coping with water deficit, for example, by breeding water retention and/or drought tolerance mechanisms into crops so that they can grow and yield under these adverse conditions.

When the rate of transpiration exceeds that of water uptake or supply, water deficit occurs and wilting symptoms appear. The responses of plants to water deficits include leaf rolling and shedding, stomata closure, leaf temperature increases, and wilting. Metabolism is also profoundly affected. General protein synthesis is inhibited and significant increases in certain amino acid pools, such as proline, become apparent (Barnett et al., 1966). During these water deficit periods, the photosynthetic rate decreases with the ultimate result of loss in yield (Boyer, 1976). If carried to an extreme, severe water deficits result in death of the plant.

Moreover, fresh water is increasingly becoming a scarce and threatened resource in large part due to agricultural production (Serageldin, 1995). Some studies have suggested that partial reduction in stomatal apertures could optimize $CO_2$ and $H_2O$ exchange, particularly in light of rising atmospheric $CO_2$ levels (Morison et al., 1987) and thus optimize $CO_2$ flow into leaves for photosynthesis and water loss through transpiration. Classical studies showed that light-induced stomatal opening is mediated by $K^+$ and anion accumulation in guard cells A network of ion channels in the plasma membrane and the vacuolar membrane of guard cells, which controls stomatal movements, has been characterized. These ion channels are targets of early signaling branches and provide probes to identify and characterize upstream transducers. Guard cell signaling integrates water status, hormonal stimuli, light, $CO_2$ levels and other environmental conditions to regulate stomatal apertures. Thus, guard cells are a well-developed model system for understanding how components interact within a signaling network in a single cell as they respond at the single cell level to physiological stimulation, allowing cell biological analyses in response to diverse stimuli. Guard cells respond to most of the classical plant hormones, which illustrates that unidentified receptors and early signaling mechanisms function in these cells.

Abscisic acid (ABA) mediates stress tolerance responses in higher plants, and is a key signal compound that regulates stomatal pore closure in leaves, a process requiring ion channel modulation by cytoplasmic proteins (Schroeder et al., 2001). Several soluble signaling proteins have been proposed to regulate guard cell ABA signal transduction (Schroeder et al., 2001). For example, the *Arabidopsis* farnesyltransferase (FTase) β subunit, encoded by ERA1, has been shown to be a negative regulator of ABA signal transduction in seeds and guard cells (Pei et al., 1998). Deletion of the ERA1 gene in *Arabidopsis* causes ABA hypersensitivity of both anion channel activation and stomatal closing, and during drought treatment era1 plants show reduced wilting and enhanced stomatal closure. Notably, when era1 plants are watered, the stomatal pores open, although to a lesser extent than in wild type, allowing $CO_2$ influx and growth. Intragenic suppressor mutants of abil-1 (abil-1R) also show reduced water loss during drought; however, era1 and abil-1R alleles have additional growth and developmental phenotypes, e.g., ERA1 null mutant plants also demonstrated slowed growth (Pei et al. 1998).

Thus, downregulation of negative regulators or upregulation of positive regulators in guard cells using guard cell-specific and stress-responsive promoters, or isolation of guard cell-specific mutants, may allow engineering of plants that lose less water during drought. Some mutations may constitutively reduce stomatal opening, which could reduce the water requirements of horticultural plants and turf grass, or in agricultural regions of marginal fresh water availability, or during drought so as to slow desiccation and damage. For plants growing in humid regions, weakening of ABA signal transduction components may enhance stomatal opening and $CO_2$ intake for carbon fixation and growth (Schroeder et al., 2001). However, conventional high-yield breeding approaches may have contributed to selection of crop plants with reduced stomatal ABA responsiveness, because genes controlling guard cell signaling are also expressed in other tissues and control other yield parameters.

Thus, what is needed is the further identification of plant genes, e.g., monocot genes, that are negative regulators of ABA signal transduction, which are useful to engineer drought hardiness into plants.

SUMMARY OF THE INVENTION

The invention relates to plants having altered, e.g., reduced, expression and/or activity of endogenous cap binding protein 80 (CBP80), including monocot CBP80, and methods of preparing and using those plants. The reduction in expression and/or activity of CBP80 in a cell may be accomplished by expression of antisense sequences, a ribozyme, RNAi, a dominant negative CBP80, or by a CBP80 gene knock out, e.g., via targeted gene disruption, and the like, which can specifically inhibit expression and/or activity of endogenous CBP80 in a host cell. Thus, the present invention provides an isolated nucleic acid molecule (polynucleotide) having a nucleotide sequence that encodes a full-length CBP80 or a fragment (portion) thereof which preferably encodes a partial-length CBP80 with substantially the same activity, e.g., at least 50%, preferably 70% and more preferably 90 to 95%, the activity, of the full-length CBP80. The nucleotide sequence preferably is obtained or isolated from a plant, for instance a monocot, DNA that encodes a polypeptide which is substantially similar, e.g., has at least 68%, 69%, and preferably has at least 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, amino acid sequence identity, to SEQ ID NO:2 or a fragment (portion) thereof which is a partial-length polypeptide having substantially the same activity as SEQ ID NO:2, and optionally includes the sequence PPTISQS (SEQ ID NO:20). In one embodiment, the nucleotide sequence encodes a CBP80 polypeptide of less than 900 residues in length and/or encodes a CBP80 polypeptide having at least 96% identity to SEQ ID NO:2.

The present invention also provides an isolated nucleic acid molecule having a nucleotide sequence, preferably obtained or isolated from monocot DNA. Preferably, the nucleotide sequence is substantially similar, i.e., has at least 65%, 66%, 67%, 68%, 69%, and preferably has at least 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, nucleic acid sequence identity, to SEQ ID NO:1, the complement thereof, a fragment (portion) thereof which encodes a partial-length polypeptide having substantially the same activity as SEQ ID NO:2, or a fragment useful to prepare a construct or vector to decrease or eliminate expression of the corresponding endogenous gene. Preferably, the term "substantially similar" when used herein with respect to a nucleotide sequence means that the nucleotide sequence is part of a gene which encodes a polypeptide having substantially the same structure and function as the polypeptide encoded by the reference nucleotide sequence. The term "substantially similar" thus includes sequences which have been modified, e.g., to optimize expression in particular cells, as well as nucleotide sequences encoding a variant polypeptide comprising one or more amino acid to substitutions relative to the (unmodified) polypeptide encoded by the reference sequence, which substitution(s) does not alter the activity of the variant polypeptide relative to the unmodified polypeptide.

Sequence comparisons may be carried out using a Smith-Waterman sequence alignment algorithm (see e.g. Waterman (1995) or on the World Wide Web at hto.usc.edu/software/segaln/index.html). The localS program, version 1.16, is preferably used with following parameters: match: 1, mismatch penalty: 0.33, open-gap penalty: 2, extended-gap penalty: 2. Further, a nucleotide sequence that is "substantially similar" to a reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

Hence, the isolated polynucleotides of the invention include the orthologs of the *Oryza sativa* sequences disclosed herein, i.e., polynucleotides in organisms other than *Oryza sativa*, including, but not limited to, monocots other than *Oryza*, preferably cereal plants, e.g., corn or wheat. An ortholog is a gene from a different species that encodes a product having the same function, e.g., catalyzes the same reaction, as the product encoded by a gene from a reference organism. Databases such GenBank may be employed to identify sequences related to the *Oryza* sequences, e.g., orthologs in cereal crops such as corn. Alternatively, recombinant DNA techniques such as hybridization or PCR may be employed to identify sequences related to the *Oryza* sequences. The encoded ortholog products likely have at least 70% sequence identity to each other. Hence, the invention includes an isolated polynucleotide comprising a nucleotide sequence encoding a polypeptide having at least 70% identity to a polypeptide encoded by the *Oryza* CBP80 sequence disclosed herein. However, an ortholog includes polypeptides having less than 65% amino acid sequence identity but which has the same or similar function as the reference polypeptide. The invention also provides antisense polynucleotides corresponding to the genes, e.g., open reading frames or fragments thereof, identified herein. Also provided are expression cassettes, e.g., recombinant vectors, and host cells, comprising the polynucleotide of the invention in either sense or antisense orientation. Thus, the present invention further provides a construct, vector or expression cassette comprising the polynucleotide of the invention, either in sense or antisense, or both, optionally linked to a promoter. The vector may be a plasmid. Such constructs, vectors or expression cassettes, when present in a plant, plant cell or plant tissue result in transcription of the linked polynucleotide in the plant and/or result in a gene knock out, so as to reduce or inhibit, and preferably eliminate, expression, of the endogenous CBP80 gene.

The constructs, expression cassettes or vectors of the invention may optionally include other regulatory sequences, e.g., transcription terminator sequences, introns and/or enhancers, and may be contained in a host cell. Preferred regulatory sequences include those which are expressed in leaf and more preferably in guard cells of a plant. Promoters for expression in guard cells include but are not limited to the KAT1 promoter (Nakamura et al., 1995), the ERA1 promoter and the ADP glucose phosphorylase promoter (Muller-Rober et al., 1994). The construct, expression cassette or vector may augment the genome of a transformed plant or may be maintained extrachromosomally. The construct, expression cassette or vector may further have a Ti plasmid and be contained in an *Agrobacterium tumefaciens* cell; it may be carried on a microparticle, wherein the microparticle is suitable for ballistic transformation of a plant cell; or it may be contained in a plant cell protoplast. Further, the construct, expression cassette or vector can be contained in a plant, plant cell or plant tissue from a dicot or a monocot. In particular, the plant may be a cereal plant.

The present invention further provides a method of augmenting a plant genome by contacting plant cells with a polynucleotide of the invention, e.g., one isolatable or obtained from a plant gene encoding a polypeptide that is substantially similar to SEQ ID NO:2, so as to yield transformed plant cells; and regenerating the transformed plant cells to provide a differentiated transformed plant, wherein the differentiated transformed plant xpresses the nucleic acid molecule in the cells of the plant. The nucleic acid molecule may be present in the nucleus, chloroplast, mitochondria and/or plastid of the cells of the plant. The present invention also provides a transgenic plant prepared by this method, a seed from such a plant and progeny plants from such a plant including hybrids and inbreds. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular nucleic acid molecule of the invention with itself or with a second plant, e.g., one lacking the particular nucleic acid molecule, to prepare the seed of a crossed fertile transgenic plant comprising the particular nucleic acid molecule. The seed is then planted to obtain a crossed fertile transgenic plant. The plant may be a monocot or a dicot. In a particular embodiment, the plant is a cereal plant.

The crossed fertile transgenic plant may have the particular nucleic acid molecule inherited through a female parent or through a male parent. The second plant may be an inbred plant. The crossed fertile transgenic may be a hybrid. Also included within the present invention are seeds of any of these crossed fertile transgenic plants.

The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

The polynucleotides of the invention, their encoded polypeptides and compositions thereof, are useful to alter abscisic acid signaling, stomatal pore opening or closing (frequency or size of opening), water loss, senescence, anion channel activity, drought tolerance, or any combination thereof, in a plant by over- or under- or knock out, of expression of CBP80. Methods to detect abscisic acid signaling, stomatal pore opening or closing, water loss, senescence, anion channel activity, or drought tolerance in a plant or plant cell are well known to the art, see, e.g., WO 01/96585. The compositions of the invention include full- or partial-length plant polynucleotides and the amino acid sequences for the full- or partial-length polypeptides encoded thereby. Methods of the invention involve stably transforming a plant with one or more of at least a portion of these polynucleotides comprising an open reading frame operably linked to a promoter capable of driving expression, e.g., antisense, of that polynucleotide in a plant cell. In another embodiment, the methods of the invention involve stably transforming a plant with a polynucleotide of the invention to yield a plant, the indogenous CBP80 gene(s) of which is disrupted, i.e., a CBP80 "knock out" plant. By "portion" or "fragment", as it relates to a nucleotide sequence of the invention, when it is linked to other sequences for expression, is meant a sequence having at least 80 nucleotides, more preferably at least 150 nucleotides, and still more preferably at least 700 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence.

The method also comprises introducing to a plant, plant cell, or plant tissue an expression cassette comprising an inhibitor of CBP80, e.g., antisense sequences, a ribozyme, RNAi, or another small molecule which specifically inhibits CBP80 or its expression, so as to yield a transformed differentiated plant, transformed cell or transformed tissue. Transformed cells or tissue can be regenerated to provide a transformed differentiated plant. The transformed differentiated plant preferably expresses the inhibitor in an amount that enhances ABA signaling in the plant, enhances stomatal closing or frequency, increases drought tolerance, increases anion channel activity, or any combination thereof. The present invention also provides a transformed plant prepared by the method, progeny and seed thereof. Further, the polynucleotide of the invention, when present in a plant in a manner which inhibits, reduces or eliminates expression of endogenous CBP80 so as to result in a drought tolerant plant, may be employed as a selectable marker.

A method to shuffle the polynucleotide of the invention is provided. This method involves fragmentation of a nucleic acid corresponding to a polynucleotide listed in SEQ ID NO:1, the orthologs thereof, and the corresponding genes, followed by religation. This method allows for the production of polypeptides having altered activity relative to the native form of the polypeptide. Accordingly, the invention provides cells and transgenic plants containing nucleic acid segments produced through shuffling that encode polypeptides having altered activity relative to the corresponding native polypeptide.

A computer readable medium, e.g., a magnetic tape, optical disk, CD-ROM, random access memory, volatile memory, non-volatile memory, or bubble memory, containing the nucleic acid sequences of the invention as well as methods of use for the computer readable medium are provided. For example, a computer readable medium can contain a nucleic acid molecule that has at least 70% nucleic acid sequence identity to SEQ ID NO:1 or the complement thereof. This medium allows a nucleic acid segment corresponding to a nucleic acid sequence listed in SEQ ID NO:1 to be used as a reference sequence to search against databases. This medium also allows for computer-based manipulation of a nucleic acid sequence corresponding to a nucleic acid sequence listed in SEQ ID NOs:1, and the corresponding gene and polypeptide encoded by the nucleic acid sequence.

DETAILED DESCRIPTION OF THE INVENTION

I. Definitions

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "protein," "peptide" and "polypeptide" are used interchangeably herein.

The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., 1991; Proudfoot, 1991; Sanfacon et al., 1991; Mogen et al., 1990; Munroe et al., 1990; Ballas et al., 1989; Joshi et al., 1987.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated. The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3'non-coding sequences) of a coding sequence, and which influence the transcription, RNA processing or stability, or translation of the associated coding sequence. Regulatory sequences include enhancers, promoters, translation-leader sequences, introns, and polyadenylation signal sequences. They include natural and synthetic sequences as well as sequences which may be a combination of synthetic and natural sequences. As is noted above, the term "suitable regulatory sequences" is n t limited to promoters.

"5'non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995). "3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5) of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

The term "intracellular localization sequence" refers to a nucleotide sequence that encodes an intracellular targeting signal. An "intracellular targeting signal" is an amino acid sequence that is translated in conjunction with a protein and directs it to a particular subs cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targeting signal. Other intracellular targeting sequences encode targeting signals active in seeds and/or leaves and "Promoter" refers to a nucleotide sequence, usually upstream (5) to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of $\geq 1\%$ of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

A commonly used procedure to analyze expression patterns and levels is through determination of the 'steady state' level of protein accumulation in a cell. Commonly used candidates for the reporter gene, known to those skilled in the art are ∃-glucuronidase (GUS), chloramphenicol acetyl transferase (CAT) and proteins with fluorescent properties, such as is green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

The term "average expression" is used here as the average level of expression found in all lines that do express detectable amounts of reporter gene, so leaving out of the analysis plants that do not express any detectable reporter mRNA or protein.

"Non-specific expression" refers to constitutive expression or low level, basal ('leaky') expression in nondesired cells or tissues from a 'regulated promoter'.

"Altered levels" refers to the level of expression in transgenic organisms that differs from that of normal or untransformed organisms.

"Overexpression" refers to the level of expression in transgenic cells or organisms that exceeds levels of expression in normal or untransformed (nontransgenic) cells or organisms.

"Antisense inhibition" refers to the production of antisense RNA transcripts capable of suppressing the expression of protein from an endogenous gene or a transgene.

"Co-suppression" and "transwitch" each refer to the production of sense RNA transcripts capable of suppressing the expression of identical or substantially similar transgene or endogenous genes (U.S. Pat. No. 5,231,020).

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English et al., 1996). Gene silencing includes virus-induced gene silencing (Ruiz et al. 1998).

"Silencing suppressor" gene refers to a gene whose expression leads to counteracting gene silencing and enhanced expression of silenced genes. Silencing suppressor genes may be of plant, non-plant, or viral origin. Examples include, but are not limited to HC-Pro, P1-HC-Pro, and 2b proteins. Other examples include one or more genes in TGMV-B genome.

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence Identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of *Arabidopsis* sequences disclosed herein. For example, altered nucleotide sequences which simply reflect the degeneracy of the genetic code but nonetheless encode amino acid sequences that are identical to a particular amino acid sequence are substantially similar to the particular sequences. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. Moreover, the skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host. "Transcription Stop Fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

"Production tissue" refers to mature, harvestable tissue consisting of non-dividing, terminally-differentiated cells. It excludes young, growing tissue consisting of germline, meristematic, and not-fully-differentiated cells.

"Germline cells" refer to cells that are destined to be gametes and whose genetic material is heritable.

"Trans-activation" refers to switching on of gene expression or replicon replication by the expression of another (regulatory) gene in trans.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include Agrobacterium-mediated transformation (De Blaere et al., 1987) and particle bombardment technology (Klein et al. 1987; U.S. Pat. No. 4,945,050). Whole plants may be regenerated from transgenic cells by methods well known to the skilled artisan (see, for example, Fromm et al., 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed in Sambrook et al., 1989. See also Innis et al., 1995 and Gelfand, 1995; and Innis and Gelfand, 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as Agrobacterium-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as Agrobacterium-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al. 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

Thus, by "variants" is intended substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%–84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, COG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest. See, for example, EPA 035472; WO 91/16432; Perlak et al., 1991; and Murray et al., 1989. In this manner, the open reading frames in genes or gene fragments can be synthesized utilizing plant-preferred codons. See, for example, Campbell and Gowri, 1990 for a discussion of host-preferred codon usage. Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, 1994; Stemmer, 1994; Crameri et al., 1997; Moore et al., 1997; Zhang et al., 1997; Crameri et al., 1998; and U.S. Pat. Nos. 5,605,793 and 5,837,458.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, 1985; Kunkel et al., 1987; U.S. Pat. No. 4,873,192; Walker and Gaastra, 1983 and the references cited therein. Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

"Vector" is defined to include, inter alia, any plasmid, cosmid, phage or Agrobactcrium binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection or cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. 1988; Higgins et al. 1989; Corpet et al. 1988; Huang et al. 1992; and Pearson et al. 1994. The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information on the World Wide Web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSIBLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more is preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point 1 for the specific sequence and its complement at a defined ionic strength and pH. However, severely stringent conditions can utilize a hybridization and/or wash at 1, 2, 3, or 4° C. lower than the thermal melting point 1; moderately stringent conditions can utilize a hybridization and/or wash at 6, 7, 8, 9, or 10° C. lower than the thermal melting point 1; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50C, more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule' is a combination of DNA sequences that are joined together using recombinant DNA technology and procedures used to join together DNA sequences as described, for example, in Sambrook et al., 1989.

The word "plant" refers to any plant, particularly to seed plant, and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

As used herein, the terms "drought resistance" and "drought tolerance" are used to refer to a plant's increased resistance or tolerance to stress induced by or in response to a reduction in water availability, as compared to normal circumstances, and the ability of the plant to function and survive in lower-water environments, and perform in a relatively superior manner. For example, the expression of an isolated and purified DNA segment encoding a gene product that alters, e.g., disrupts, inhibits or eliminates, ABA signal transduction in a plant likely regulates the activity of guard cell stomata and imparts protection to the plant against drought.

II. The Polynucleotides of the Invention and the Polypeptides Encoded Thereby

This invention relates to an isolated plant, e.g., *Oryza sativa*, polynucleotide, i.e., a nucleic acid molecule, sequence or segment (fragment), which encodes a monocot cap binding protein 80. The polynucleotide can, for example, be used to prepare constructs which overexpress the encoded protein or a variant thereof, to prepare antisense constructs, to prepare constructs to knock out the expression of at least one genomic copy of the gene, or to prepare constructs comprising a ribozyme or RNAi specific for cap binding protein 80.

Sources for the polynucleotide of the invention include dicots and monocots, including but not limited to, corn (*Zea mays*), Brassica sp. (e.g., *B. napus, B. rapa, B. juncea*), particularly those *Brassica* species useful as sources of seed oil, alfalfa (*Medicago saliva*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers; duckweed (Lemna, see WO 00/07210, which includes members of the family Lemnaceae.

There are known four genera and 34 species of duckweed as follows: genus Lemna (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus Spirodela (*S. intermedia, S. polyrrhiza, S. punctata*); genus Woffia (*Wa. angusia, Wa.* arrhiza, *Wa. australina, Wa. borealis, Wa. brasiliensis, Wa. columbiana, Wa. elongata, Wa. globosa, Wa. microscopica, Wa. neglecia*) and genus *Wofiella* (*Wl. caudata, Wl. denticulata, Wl. gladiata, Wl. hyalina, Wl. lingulara, Wl. repunda, Wl. rotunda*, and *Wl. neotropica*). Any other genera or species of Lemnaceae, if they exist, are also aspects of the present invention. *Lemna gibba, Lemna minor*, and *Lemna miniscula* are preferred, with *Lemna minor* and *Lemna miniscula* being most preferred. *Lemna* species can be classified using the taxonomic scheme described by Landolt, Biosystematic Investigation on the Family of Duckweeds: The family of Lemnaceae—A Monograph Study. Geobotanisches Institut ETH, Stiftung Rubel, Zurich (1986)); vegetables including tomatoes (*Lycopersicon esculentum*), lettuce (e.g., *Lactuca sativa*), green beans (*Phaseolus vulgaris*), lima beans (*Phaseolus limensis*), peas (*lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*); and leguminous plants.

Leguminous plants include beans and peas. Beans include guar, locust bean, fenugreek, soybean, garden beans, cowpea, mungbean, lima bean, fava bean, lentils, chickpea, etc. Legumes include, but are not limited to, Arachis, e.g., peanuts, Vicia, e.g., crown vetch, hairy vetch, adzuki bean, mung bean, and chickpea, Lupinus, e.g., lupine, trifolium, Phaseolus, e.g., common bean and lima bean, Pisum, e.g., field bean, Melilotus, e.g., clover, Medicago, e.g., alfalfa, Lotus, e.g., trefoil, lens, e.g., lentil, and false indigo. Other sources for the polynucleotides of the invention include Acacia, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, Brassica, e.g., broccoli, cabbage, brussel sprouts, onion, carrot, leek, beet, broad bean, celery, radish, pumpkin, endive, gourd, garlic, snapbean, spinach, squash, turnip, asparagus, and zucchini and ornamental plants include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia.

Other vegetable sources (and databases to identify orthologs of the invention) for the nucleic acid sequences of the invention include Cucurbitaceae, e.g., *Cucumis sativus, Cucumis melo, Citrullus lanatus, Cucurbila pepo, Cucurbita maxima*, and *Cucurbita moschata* (see the World Wide Web at cucurbit.org/, genome.cornell.edu/cgc/or nal.usda.gov/pgdic/Map_proj/); Solanaceae, e.g., *Lycopersicon esculentum, Capsiewn annuum, Capsicum frutescens, Solinum melongena, Nicotiana tabacum, Solanum tuberosum*, Petuniax hybrida hort. ex E. Vilm. (see, 15×BAC on variety Heinz 1706 order from Clemson Genome center on the World Wide Web at genome.clemson.edu, 11.6×BAC of *L. cheesmanii* (originates from *J. Giovannoni*) available from Clemson genome center on the World Wide Web at genome.clemson.edu, EST collection from TIGR on the World Wide Web at tigr.org/tdb/lgi/index.html, EST collection from Clemson Genome Center on the World Wide Web at genome.clemson.edu, esculentum×pennelli peruvianum, potato×tomato, potato and tomato, esculentum×pennelli isozyme and cDNAs, 4×BAC of Petunia hybrida 7984 available from Clemson genome center on the World Wide Web at genome.clemson.edu, genome.cornell.edu/solgenes, ars-genome.cornell.edu/cgi-bin/WebAce/webace?db=solgenes, genome.cornell.edu/tgc/, tgrc.ucdavis.edu, neptune.netimages.com/.about.chile/science.html, and nal.usda.gov/pgdic/Map_proi.; Brassicaceae, e.g., *Brassica oleracea* L. var. *italica, Brassica oleracea* L. var. *capitata, Brassica rapa, Brassica oleracea* L. var. *botrytis, Raphanus sativus* var. *niger*, and *Brassica napus* (see, 12× and 6×BACs on Columbia strain available from the following World Wide Web sites: genome.clemson.edu (Clemson genome center), res.agr.ca/ecorc/cwmt/crucifer/traits/index.htm, geneous.cit-.cornell.edu/cabbage/aboutcab.html, ars-genome.comell.edu/cgi-bin/WebAce/webace?db=brassicadb, ars-genome.comell.edu/cgi-bin/WebAce/webace?db=agr, nal.usda.gov/pgdic/MAP_proj/; Umbelliferae, e.g., *Daucus carota*, Compositae, e.g., *Lactuca sativa*, and *Helianthus annuus*; Chenopodiaceac, e.g., *Spinacia oleracea* and *Beta vulgaris*; Leguminosae, e.g., *Phaseolus vulgas, Pisum sativum*, and *Glycine max* (see, 4.3×BAC available from Clemson genome center on the World Wide Web at gcnome.clemson.edu, 7.5× and 7.9×BACs available from the following World Wide Web sites: genome.clemson.edu, nal.usda.gov/pgdic/Map_proj/, ars-genome.cornell.edu/cgi-bin/webAce/webace?db=beangenes, or ars-genome.comell.edu/cgi-bin/WebAce/webace?db=soybase; Gramineae, e.g., *Zea mays*, see, Novartis BACs for Mo 17 and B73 have been donated to Clemson Genome Center and are available at the following World Wide Web sites: genome.clemson.edu, nal.usda.gov/pgdic/Map_proj/, and agron.missouri.ed-u/mnl/; or Liliaceae, e.g., *Allium cepa* (see, the World Wide Web site nal.usda.gov/pgdi-c/Map_proj/.

Preferred forage and turf grass nucleic acid sources for the polynucleotides of the invention include alfalfa, orchard grass, tall fescue, perennial ryegrass, creeping bent grass, and redtop. Preferably, the nucleic acid sources are crop plants and in particular cereals, e.g., wheat, rice, corn, oats, barley, and rye, and even more preferably rice, corn and wheat.

Based on the *Oryza* nucleotide sequence of the present invention, orthologs may be identified or isolated from the genome of any desired organism, preferably from another plant, according to well known techniques based on their sequence similarity to the *Oryza* nucleic acid sequences, e.g., hybridization, PCR or computer generated sequence comparisons. For example, all or a portion of a particular *Oryza* nucleotide sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook et al., 1989) and amplification by PCR using oligonucleotide primers preferably corresponding to sequence domains conserved among related polypeptide or subsequences of the nucleotide sequences provided herein (see, e.g., Innis et al., 1995). These methods are particularly well suited to the isolation of gene sequences from organisms closely related to the organism from which the probe sequence is derived.

The application of these methods using the *Oryza* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al., 1989. In general, sequences that hybridize to the sequences disclosed herein will have at least 40% to 50%, about 60% to 70% and even about 80% 85%, 90%, 95% to 98% or more identity with the disclosed sequences. That is, the sequence similarity of sequences may range, sharing at least about 40% to 50%, about 60% to 70%, and even about 80%, 85%, 90%, 95% to 98% sequence similarity.

The polynucleotides of the invention can also be identified by, for example, a search of known databases for genes encoding polypeptides having a specified amino acid sequence identity. Methods of alignment of sequences for comparison are well known in the art and are described hereinabove.

III. DNA Sequences for Transformation

Virtually any DNA composition may be used for delivery to recipient plant cells, e.g., monocotyledonous cells, to ultimately produce fertile transgenic plants in accordance with the present invention. For example, DNA segments in the form of vectors and plasmids, or linear DNA fragments, in some instances containing only the DNA element to be expressed in the plant, and the like, may be employed. The construction of vectors which may be employed in conjunction with the present invention will be known to those of skill of the art in light of the present disclosure (see, e.g., Sambrook et al., 1989; Gelvin et al., 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., 1991). These vectors are capable of autonomous replication in maize cells as well as *E. coli*, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs et al., 1990) that transposition of these elements within the maize genome requires DNA replication. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable or the undesirable DNA sequences.

DNA useful for introduction into plant cells includes that which has been derived or isolated from any source, that may be subsequently characterized as to structure, size and/or function, chemically altered, and later introduced into plants. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Such DNA is commonly referred to as "recombinant is DNA."

Therefore useful DNA includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced DNA includes but is not limited to, DNA from plant genes, and non-plant genes such as those from bacteria, yeasts, animals or viruses. The introduced DNA can include modified genes, portions of genes, or chimeric genes, including genes from the same or different maize genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant. For example, the DNA may itself comprise or consist of a promoter that is active in a plant which is derived from a source other than that plant, or may utilize a promoter already present in a plant genotype that is the transformation target.

Generally, the introduced DNA will be relatively small, i.e., less than about 30 kb to minimize any susceptibility to physical, chemical, or enzymatic degradation which is known to increase as the size of the DNA increases. As noted above, the number of proteins, RNA transcripts or mixtures thereof which is introduced into the plant genome is preferably preselected and defined, e.g., from one to about 5–10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters.

Promoters which are useful for plant transgene expression include those that are inducible, viral, synthetic, constitutive (Odell et al., 1985), temporally regulated, spatially regulated, tissue-specific, and spatio-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A. Transcription Regulatory Sequences

1. Promoters

The choice of promoter will vary depending on the temporal and spatial requirements for expression, and also depending on the target species. In some cases, expression in multiple tissues is desirable. While in others, tissue-specific, e.g., leaf-specific, seed-specific, petal-specific, anther-specific, or pith-specific, expression is desirable. Although many promoters from dicotyledons have been shown to be operational in monocotyledons and vice versa, ideally dicotyledonous promoters are selected for expression in dicotyledons, and monocotyledonous promoters for expression in monocotyledons: However, there is no restriction to the provenance of selected promoters; it is sufficient that they are operational in driving the expression of the nucleotide sequences in the desired cell.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{lac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

A range of naturally-occurring promoters are known to be operative in plants and have been used to drive the expression of heterologous (both foreign and endogenous) genes in plants: for example, the constitutive 35S cauliflower mosaic virus (CaMV) promoter, the ripening-enhanced tomato polygalacturonase promoter (Bird et al., 1988), the E8 promoter (Diekman & Fischer, 1988) and the fruit specific 2A1 promoter (Pear et al., 1989) and many others, e.g., U2 and U5 mRNA promoters from maize, the promoter from alcohol dehydrogenase, the Z4 promoter from a gene encoding the Z422 kD zein protein, the Z10 promoter from a gene encoding a 10 kD zein protein, a Z27 promoter from a gene encoding a 27 kD zein protein, the A20 promoter from the gene encoding a 19 kcD-zein protein, inducible promoters, such as the light inducible promoter derived from the pea rbcS gene and the actin promoter from rice, e.g., the actin 2 promoter (WO 00/70067); seed specific promoters, such as the phaseolin promoter from beans, may also be used. The nucleotide sequences of this invention can also be expressed under the regulation of promoters that are chemically regulated. This enables the nucleic acid sequence or encoded polypeptide to be synthesized only when the crop plants are treated with the inducing chemicals. Chemical induction of gene expression is detailed in EP 0 332 104 (to Ciba-Geigy) and U.S. Pat. No. 5,614,395. A preferred promoter for chemical induction is the tobacco PR-1a promoter.

Examples of some constitutive promoters which have been described include the rice actin 1 (Wang et al., 1992; U.S. Pat. No. 5,641,876), CaMV 35S (Odell et al., 1985), CaMV 19S (Lawton et al., 1987), nos, Adh, sucrose synthase; and the ubiquitin promoters.

Examples of tissue specific promoters which have been described include the lectin (Vodkin, 1983; Lindstrom et al., 1990) corn alcohol dehydrogenase 1 (Vogel et al., 1989; Dennis et al., 1984), corn light harvesting complex (Simpson, 1986; Bunsal et al., 1992), corn heat shock protein (Odell et al., 1985), pea small subunit RuBP carboxylase (Poulsen et al., 1986), Ti plasmid mannopine synthase (Langridge et al., 1989), Ti plasmid nopaline synthase (Langridge et al., 1989), petunia chalcone isomerase (van-Tunen et al., 1988), bean glycine rich protein 1 (Keller et al., 1989), truncated CaMV 35s (Odell et al., 1985), potato patatin (Wenzler et al., 1989), root cell (Yamamoto et al., 1990), maize zein (Reina et al., 1990; Kriz et al., 1987; Wandelt et al., 1989; Langridge et al., 1983; Reina et al., 1990), globulin-1 (Belanger et al., 1991), α-tubulin, cab (Sullivan et al., 1989), PEPCase (Hudspeth & Grula, 1989), R gene complex-associated promoters (Chandler et al., 1989), histone, and chalcone synthase promoters (Franken et al., 1991). Tissue specific enhancers are described in Fromm et al. (1989).

Inducible promoters that have been described include the ABA- and turgor-inducible promoters, the promoter of the auxin-binding protein gene (Schwob et al., 1993), the UDP glucose flavonoid glycosyl-transferase gene promoter (Ralston et al., 1988), the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989).

Several other tissue-specific regulated genes and/or promoters have been reported in plants. These include genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase. And fatty acid desaturases (fad 2-1)), and other genes expressed during embryo development (such as Bce4, see, for example, EP 255378 and Kridl et al., 1991). Particularly useful for seed-specific expression is the pea vicilin promoter (Czako et al., 1992). (See also U.S. Pat. No. 5,625,136, herein incorporated by reference.) Other useful promoters for expression in mature leaves are those that are switched on at the onset of senescence, such as the SAG promoter from *Arabidopsis* (Gan et al., 1995). .

A class of fruit-specific promoters expressed at or during antithesis through fruit development, at least until the beginning of ripening, is discussed in U.S. Pat. No. 4,943,674. cDNA clones that are preferentially expressed in cotton fiber have been isolated (John et al., 1992). cDNA clones from tomato displaying differential expression during fruit development have been isolated and characterized (Mansson et al., 1985, Slater et al., 1985). The promoter for polygalacturonase gene is active in fruit ripening. The polygalacturonase gene is described in U.S. Pat. Nos. 4,535,060, 4,769,061, 4,801,590, and 5,107,065, which disclosures are incorporated herein by reference.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., 1992). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., 1997). Other tissue-specific promoters can be isolated by one skilled in the art (see U.S. Pat. No. 5,589,379). Several inducible promoters ("gene switches") have been reported. Many are described in the review by Gatz (1996) and Gatz (1997). These include tetracycline repressor system, Lac repressor system, copper-inducible systems, salicylate-inducible systems (such as the PR1a system), glucocorticoid (Aoyama et al., 1997) and ecdysone-inducible systems. Also included are the benzene sulphonamide (U.S. Pat. No. 5,364,780) and alcohol-(WO 97/06269 and WO 97/06268) inducible systems and glutathione S-transferase promoters. Other studies have focused on genes inducibly regulated in response to environmental stress or stimuli such as increased salinity. Drought, pathogen and wounding. (Graham et al., 1985; Graham et al., 1985, Smith et al., 1986). Accumulation of metallocarboxypeptidase-inhibitor protein has been reported in leaves of wounded potato plants (Graham et al., 1981). Other plant genes have been reported to be induced methyl jasmonate, elicitors, heat-shock, anaerobic stress, or herbicide safeners.

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant to infection by soil- and airborne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive, tissue-independent promoter operably linked to an antisense nucleotide sequence, such that constitutive expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulinI promoter, an actin I promoter, an actin cI promoter, a sucrose synthetase promoter, an INOPS promoter, an EXM5 promoter, a globulin2 promoter, a b-32, ADPG-pyrophosphorylase promoter, an LtpI promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter (Huffman), an anther-specific gene RTS2 promoter, a pollen-specific gene promoter, a tapetum-specific gene promoter, tapetum-specific gene RAB24 promoter, a anthranilate synthase alpha subunit promoter, an alpha zein promoter, an anthranilate synthase beta subunit promoter. a dihydrodipicolinate synthase promoter, a ThiI promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase Sadenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

2. Other Regulatory Elements

In addition to promoters, a variety of 5N and 3N transcriptional regulatory sequences are also available for use in the present invention. Transcriptional terminators are responsible for the termination of transcription and correct mRNA polyadenylation. The 3N nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CAMV 35S terminator, the tml terminator, the nopaline synthase terminator, the pea rbcS E9 terminator, the terminator for the T7 transcript from the octopine synthase gene of *Agrobacterium tumefaciens*, and the 3N end of the protease inhibitor I or II genes from potato or tomato, although other 3N elements known to those of skill in the art can also be employed. Alternatively, one also could use a gamma coixin, oleosin 3 or other terminator from the genus Coix.

Preferred 3' elements include those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor 1 or 11 genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Other sequences that have been found to enhance gene expression in transgenic plants include intron sequences (e.g.; from Adh1, bronze1, actin1, actin 2 (WO 00/760067), or the sucrose synthase intron) and viral leader sequences (e.g., from TMV, MCMV and AMV). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie et al., 1987; Skuzeski et al., 1990). Other leaders known in the art include but are not limited to: Picornavirus leaders, for example, EMCV leader (Encephalomyocarditis 5 noncoding region) (Elroy-Stein et al., 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak et al., 1991); Untranslated leader from the coat protein mRNA of alfalfa mosaic virus (AMV RNA 4), (Jobling et al., 1987; Tobacco mosaic virus leader (TMV), (Gallie et al., 1989; and Maize Chlorotic Mottle Virus leader (MCMV) (Lommel et al., 1991. See also, Della-Cioppa et al., 1987.

Regulatory elements such as Adh intron 1 (Callis et al., 1987), sucrose synthase intron (Vasil et al., 1989) or TMV omega element (Gallie, et al., 1989), may further be included where desired.

Examples of enhancers include elements from the CAMV 35S promoter, octopine synthase genes (Ellis et al., 1987), the rice actin I gene, the maize alcohol dehydrogenase gene (Callis et al., 1987), the maize shrunken I gene (Vasil et al., 1989), TMV Omega element (Gallie et al., 1989) and promoters from non-plant eukaryotes (e.g. yeast; Ma et al., 1988).

Vectors for use in accordance with the present invention may be constructed to include the ocs enhancer element. This element was first identified as a 16 bp palindromic enhancer from the octopine synthase (ocs) gene of ultilane (Ellis et al., 1987), and is present in at least 10 other promoters (Bouchez et al., 1989). The use of an enhancer element, such as the ocs element and particularly multiple copies of the element, will act to increase the level of transcription from adjacent promoters when applied in the context of monocot transformation.

Ultimately, the most desirable DNA segments for introduction into for example a monocot genome may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting of a gene in a constitutive manner or a root-specific manner. For example, insect resistant genes may be expressed specifically in the whorl and collar/sheath tissues which are targets for the first and second broods, respectively, of ECB. Likewise, genes encoding proteins with particular activity against rootworm may be targeted directly to root tissues.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an alpha-tubulin gene that directs expression in roots and promoters derived from zein storage protein genes which direct expression in endosperm. It is particularly contemplated that one may advantageously use the 16 bp ocs enhancer element from the octopine synthase (ocs) gene (Ellis et al., 1987; Bouchez et al., 1989), especially when present in multiple copies, to achieve enhanced expression in roots.

Tissue specific expression may be functionally accomplished by introducing a constitutively expressed gene (all tissues) in combination with an antisense gene that is expressed only in those tissues where the gene product is not desired. For example, a gene coding for the crystal toxin protein from *B. thuringiensis* (Bt) may be introduced such that it is expressed in all tissues using the 35S promoter from Cauliflower Mosaic Virus. Expression of an antisense transcript of the Bt gene in a maize kernel, using for example a zein promoter, would prevent accumulation of the Bt protein in seed. Hence the protein encoded by the introduced gene would be present in all tissues except the kernel.

Expression of some genes in transgenic plants will be desired only under specified conditions. For example, it is proposed that expression of certain genes that confer resistance environmental stress factors such as drought will be desired only under actual stress conditions. It is contemplated that expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It is also anticipated that expression of genes conferring resistance to insect predation would be desired only under conditions of actual insect infestation. Therefore, for some desired traits inducible expression of genes in transgenic plants will be desired.

Expression of a gene in a transgenic plant will be desired only in a certain time period during the development of the plant. Developmental timing is frequently correlated with tissue specific gene expression. For example, expression of zein storage proteins is initiated in the endosperm about 15 days after pollination.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell.

Other elements include those that can be regulated by endogenous or exogenous agents, e.g., by zinc finger proteins, including naturally occurring zinc finger proteins or chimeric zinc finger proteins (see, e.g., U.S. Pat. No. 5,789, 538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences which bind to a specific DNA sequence (the zinc finger) and amino acid sequences that activate (e.g., GAL 4 sequences) or repress the transcription of the sequences linked to the specific DNA sequence.

3. Methods for Mutagenizing DNA

It is specifically contemplated by the inventors that one could mutagenize DNA having a promoter or open reading frame to, for example, potentially improve the utility of the DNA for expression of transgenes in plants. The mutagenesis can be carried out at random and the mutagenized sequences screened for activity in a trial-by-error procedure. Alternatively, particular sequences which provide the promoter with desirable expression characteristics, or a promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment of the current invention are well-known to those of skill in the art. As indicated, modifications may be made by random or site-specific mutagenesis procedures. The DNA may be modified by altering its structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art.

Double stranded plasmids also are routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation.

This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

In addition, an unmodified or modified nucleotide sequence of the present invention can be varied by shuffling the sequence of the invention. To test for a function of variant DNA sequences according to the invention, the sequence of interest is operably linked to a selectable or screenable marker gene and expression of the marker gene is tested in transient expression assays with protoplasts or in stably transformed plants. It is known to the skilled artisan that DNA sequences capable of driving expression of an associated nucleotide sequence are build in a modular way. Accordingly, expression levels from shorter DNA fragments may be different than the one from the longest fragment and may be different from each other. For example, deletion of a down-regulating upstream element will lead to an increase in the expression levels of the associated nucleotide sequence while deletion of an up-regulating element will decrease the expression levels of the associated nucleotide sequence. It is also known to the skilled artisan that deletion of development-specific or a tissue-specific element will lead to a temporally or spatially altered expression profile of the associated nucleotide sequence.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Ramstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different deletion mutants of the starting promoter could be readily prepared.

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

B. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PRS).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel et al., 1990) molecule is well characterized in terms of molecular biology, expression and protein to structure. However, any one of a variety of ultilane and/or glycine-rich wall proteins (Keller et al., 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

1. Selectable Markers

Possible selectable markers for use in connection with the present invention include, but are not limited to, a neo gene which codes for kanamycin resistance and can be selected for using kanamycin, G418, paromomycin, and the like; a bar gene which codes for bialaphos or phosphinothricin resistance; a gene which encodes an altered EPSP synthase protein (Hinchee et al., 1988) thus conferring glyphosate resistance; a nitrilase gene such as bxn from Klebsiella ozaenae which confers resistance to bromoxynil (Stalker et al., 1988); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon; a mutated anthranilate synthase gene that confers resistance to 5-methyl tryptophan. Preferred selectable marker genes encode phosphinothricin acetyltransferase; glyphosate resistant EPSPS, aminoglycoside phosphotransferase; hygromycin phosphotransferase, or neomycin phosphotransferase. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals.

Where one desires to employ a bialaphos resistance gene in the practice of the invention, a particularly useful gene for this purpose is the bar or pat genes obtainable from species of Streptomyces (e.g., ATCC No. 21,705). The cloning of the bar gene has been described (Murakami et al., 1986; Thompson et al., 1987) as has the use of the bar gene in the context of plants other than monocots (De Block et al., 1987; De Block et al., 1989).

Selection markers resulting in positive selection, such as a phosphomannose isomerase gene, as described in patent application WO 93/05163, may also be used. Alternative genes to be used for positive selection are described in WO 94/20627 and encode xyloisomerases and phosphomannoisomerases such as mannose-6-phosphate isomerase and mannose-1'-phosphate isomerase; phosphomanno mutase; mannose epimerases such as those which convert carbohydrates to mannose or mannose to carbohydrates such as glucose or galactose; phosphatases such as man nose or xylose phosphatase, mannose-6-phosphatase and mannose-1-phosphatase, and permeases which are involved in the transport of mannose, or a derivative, or a precursor thereof into the cell. Transformed cells are identified without damaging or killing the non-transformed cells in the population and without co-introduction of antibiotic or herbicide resistance genes. As described in WO 93/05163, in addition to the fact that the need for antibiotic or herbicide resistance genes is eliminated, it has been shown that the positive selection method is often far more efficient than traditional negative selection.

2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a beta-lactamase gene (Sutcliffe, 1978), which encodes an enzyme for which various chromogenic substrates are known (e.g., PADAC, a chromogenic cephalosporin); a xyle gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is carries dominant ultila for genes encoding the enzymatic intermediates in the anthocyanin biosynthetic pathway (C2, A1, A2, Bz1 and Bz2) (Roth et al., 1990), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bo13). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

C. Exogenous Genes for Modification of Plant Phenotypes

Genes of interest are reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest which encodes a polypeptide are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used. For examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvyishikimate 3-phosphate synthase (EPSP Synthase), is normally inhibited by the herbicide N-(phosphonomethyl)glycine (glyphosate). However, genes are known that encode glyphosate-resistant EPSP Synthase enzymes.

These genes are particularly contemplated for use in monocot transformation. The deh gene encodes the enzyme dalapon dehalogenase and confers resistance to the herbicide dalapon. The bxn gene codes for a specific nitrilase enzyme that converts bromoxynil to a non-herbicidal degradation product.

2. Insect Resistance

An important aspect of the present invention concerns the introduction of insect resistance-conferring genes into plants. Potential insect resistance genes which can be introduced include *Bacillus thuringiensis* crystal toxin genes or Bt genes (Watrud et al., 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA(c) genes. Endotoxin genes from other species of *B. thuringiensis* which affect insect growth or development may also be employed in this regard.

The poor expression of Bt toxin genes in plants is a well-documented phenomenon, and the use of different promoters, fusion proteins, and leader sequences has not led to significant increases in Bt protein expression (Vaeck et al., 1989; Barton et al., 1987). It is therefore contemplated that the most advantageous Bt genes for use in the transformation protocols disclosed herein will be those in which the coding sequence has been modified to effect increased expression in plants, and more particularly, those in which maize preferred codons have been used. Examples of such modified Bt toxin genes include the variant Bt CryIA(b) gene termed Iab6 (Perlak et al., 1991) and the synthetic CryIA(c) genes termed 1800a and 1800b.

Protease inhibitors may also provide insect resistance (Johnson et al., 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by oryzacystatin and amylase inhibitors, such as those from wheat and barley.

Also, genes encoding lectins may confer additional or alternative insecticide propenies. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla and Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, may also result in insecticidal activity, or perhaps cause cessation of metamorphosis (Hammock et al., 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn et al., 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, 1972).

Further genes encoding proteins characterized as having potential insecticidal activity may also be used as transgenes in accordance herewith. Such genes include, for example, the cowpea trypsin inhibitor (CPTI; Hilder et al., 1987) which may be used as a rootworm deterrent; genes encoding avermectin (Campbell, 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

3. Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "anti-freeze" protein such as that of the Winter Flounder (Cutler et al., 1989) or synthetic gene derivatives thereof. Improved chilling tolerance may also be conferred through increased expression of glycerol-3-phosphate acetyltransferase in chloroplasts (Murata et al., 1992; Wolter et al., 1992). Resistance to oxidative stress (often exacerbated by conditions such as chilling temperatures in combination with high light intensities) can be conferred by expression of super-oxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically-active solutes can impart protection against drought. Within this class of genes are DNAs encoding mannitol dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., cited supra (1992), 1993).

Similarly, the efficacy of other metabolites in protecting either enzyme function (e.g. alanopine or propionic acid) or membrane integrity (e.g., alanopine) has been documented (Loomis et al., 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), ononitol and pinitol (Vernon and Bohnert, 1992), and raffinose (Bernal-Lugo and Leopold, 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol O-methyltransferase.

It is contemplated that the expression of specific proteins may also increase drought tolerance. Three classes of Late Embryogenic Proteins have been assigned based on structural similarities (see Dure et al., 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero et al., 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al. 1990 and Shagan et al., 1993). Spatial and temporal expression patterns of these genes may enable maize to better withstand stress.

Expression of genes that are involved with specific morphological traits that allow for increased waler extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan et al., *Science,* 270:1986 (1995)).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

4. Disease Resistance

It is proposed that increased resistance to diseases may be realized through introduction of genes into plants period. It is possible to produce resistance to diseases caused by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol et al., 1990). Included amongst the PR proteins are beta1,3-glucanases, chitinases, and osmotin and other proteins that are believed to function in plant resistance to disease organisms. Other genes have been identified that have antifungal properties, e.g., UDA (stinging nettle lectin) and hevein (Broakgert et al., 1989; Barkai-Golan et al., 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

5. Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

6. Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring et al., 1991). Additionally, the introduced DNA may encode enzymes which degrade seines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other well known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

7. Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plant of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. Overexpression of genes within plants that are associated with "stay green" or the expression of any gene that delays senescence would be advantageous. For example, a non-yellowing mutant has been identified in Festuca pratensis (Davies et al., 1990). Expression of this gene as well as others may prevent premature breakdown of chlorophyll and thus maintain canopy function.

8. Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

9. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al, 1990).

For example, a number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

10. Negative Selectable Markers

Introduction of genes encoding traits that can be selected against may be useful for eliminating undesirable linked genes. When two or more genes are introduced together by cotransformation, the genes will be linked together on the host chromosome. For example, a gene encoding a Bt gene that confers insect resistance on the plant may be introduced into a plant together with a bar gene that is useful as a selectable marker and confers resistance to the herbicide Ignite® on the plant. However, it may not be desirable to have an insect resistant plant that is also resistant to the herbicide Ignite®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

Negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (nptII) has been investigated as a negative selectable marker in tobacco (Nicotiana tabacum) and Arabidopsis thaliana (Xiang and Guerra, 1993). In this example both sense and antisense nptII genes are introduced into a plant through transformation and the resultant plants arc sensitive to (tic antibiotic kanamycin. An introduced gene that integrates into the host cell chromosome at the site of the antisense nptII gene, and inactivates the antisense gene, will make the plant resistant to kanamycin and other aminoglycoside antibiotics. Therefore, rare site specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers may also be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, 1993). In the presence of this enzyme the compound 5-fluorocytosine is converted to 5-fluoruracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from Agrobacterium tumefaciens encodes a protein that catalyzes the conversion of alpha-naphthalene acetamide (NAM) to alpha-napthalene acetic acid (NAA) renders plant cells sensitive to high concentrations of NAM (Depicker et al., 1988).

It is also contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

11. Non-Protein-Expressing Sequences a. RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA. It is also possible that genes may be introduced to produce novel transgenic plants which have reduced expression of a native gene product by a mechanism of cosuppression. It has been demonstrated in tobacco, tomato, and petunia (Goring et al, 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

b. Non-RNA-Expressing

For example, DNA elements including those of transposable elements such as Ds, Ac, or Mu, may be inserted into a gene and cause mutations. These DNA elements may be inserted in order to inactivate (or activate) a gene and thereby "tag" a particular trail. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm Another possible element which may be introduced is a matrix attachment region element (MAR), such as the chicken lysozyme A element (Stief et al., 1989), which can be positioned around an expressible gene of interest to effect an increase in overall expression of the gene and diminish position dependant effects upon incorporation into the plant genome (Stief et al., 1989; Phi-Van et al., 1990).

IV. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invent ion may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*) cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamida (*Macadamia integrifolia*), almond (*Prunus amygdalus*), sugar beets (*Beta vulgaris*), sugarcane (*Saccharum* spp.), oats, barley, vegetables, ornamentals, and conifers; duckweed (Lemna, see WO 00/072 10, which includes members of the family Lemnaceae.

There are known four genera and 34 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Woffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus *Wofiella* (*Wl. caudata, Wl. denticulata, Wl. gladiata, Wl. hyalina, Wl. lingulata, Wl. repunda, Wl. rotunda,* and *Wl. neotropica*). Any other genera or species of *Lemnaceae*, if they exist, are also aspects of the present invention. *Lemna gibba, Lemna minor*, and *Lemna miniscula* are preferred, with *Lemna minor* and *Lemna miniscula* being most preferred. *Lemna* species can be classified using the taxonomic scheme described by Landolt, Biosystematic Investigation on the Family of Duckweeds: The family of Lemnaceae—A Monograph Study. Geobotanisches Institut ETH, Stiftung Rubel, Zurich (1986)); vegetables including tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*); and leguminous plants.

Leguminous plants include beans and peas. Beans include guar, locust bean, fenugreek, soybean, garden beans, cowpea, mungbean, lima bean, fava bean, lentils, chickpea, etc. Legumes include, but are not limited to, Arachis, e.g., peanuts, Vicia, e.g., crown vetch, hairy vetch, adzuki bean, mung bean, and chickpea, Lupinus, e.g., lupine, trifolium, Phaseolus, e.g., common bean and lima bean, Pisum, e.g., field bean, Melilotus, e.g., clover, Medicago, e.g., alfalfa, Lotus, e.g., trefoil, lens, e.g., lentil, and false indigo. Other sources for the polynucleotides of the invention include Acacia, aneth, artichoke, arugula, blackberry, canola, cilantro, clementines, escarole, eucalyplus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, Brassica, e.g., broccoli, cabbage, brussel sprouts, onion, carrot, leek, beet, broad bean, celery, radish, pumpkin, endive, gourd, garlic, snapbean, spinach, squash, turnip, asparagus, and zucchini and ornamental plants include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia.

Other plants for transformation include Cucurbitaceae, e.g., *Cucumis sativus, Cucumis melo, Citrullus lanatus, Cucurbita pepo, Cucurbita maxima,* and *Cucurbita moschata*; Solanaceae, e.g., *Lycopersicon esculentum, Capsicum annuum, Capsicum frutescens, Solanum melongena, Nicotiana tabacum, Solanum tuberosum*, Petunia×hybrida hort. ex E. Vilm. Brassicaceae, e.g., *Brassica oleracea* L. var. *italica, Brassica oleracea* L var. *capitata, Brassica rapa, Brassica oleracea* L. var. *botrytis, Raphanus sativus* var. *niger,* and *Brassica napus*; Umbelliferae, e.g., *Daucus carota*, Compositae, e.g., *Lactuca sativa,* and *Helianthus annuus*; Chenopodiaceae, e.g., *Spinacia oleracea* and *Beta vulgaris*; Leguminosae, e.g., *Phaseolus vulgaris, Pisum sativum,* and *Glycine max*; Gramineae, e.g., *Zea mays*; or Liliaceae, e.g., *Allium cepa*.

Preferred forage and turf grass plants for transformation include alfalfa, orchard grass, tall fescue, perennial ryegrass, creeping bent grass, and redtop. Preferably, the plants are crop plants and in particular cereals, e.g., wheat, rice, corn, oats, barley, and rye, and even more preferably rice, corn and wheat.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tunefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al., (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al., (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues, (Lindsey et al., 1993; Auch & Reth et al.).

It is particularly preferred to use the binary type vectors of Ti and R1 plasmids of Agrobacterium spp. Ti-derived vectors transform a wide variety of higher plants, including monocotyledonous and dicotyledonous plants, such as soybean, cotton, rape, tobacco, and rice (Pacciotti et al., 1985: Byrne et al., 1987; Sukhapinda et al., 1987; Park et al., 1985: Hiei et al., 1994). The use of T-DNA to transform plant cells has received extensive study and is amply described (EP 120516; Hoekema, 1985; Knauf, et al., 1983; and An et al., 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm et al., 1986) or high velocity ballistic bombardment with metal particles coated with the nucleic acid constructs (Kline et al., 1987, and U.S. Pat. No. 4,945,050). Once transformed, the cells can be regenerated by those skilled in the art. Of particular relevance are the recently described methods to transform foreign genes into commercially important crops, such as rapeseed (De Block et al., 1989), sunflower (Everett et al., 1987), soybean (McCabe et al., 1988; Hinchee et al., 1988; Chee et al., 1989; Christou et al., 1989; EP 301749), rice (Hiei et al., 1994), and corn (Gordon Kamm et al., 1990; Fromm et al., 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway et al., 1986), electroporation (Riggs et al., 1986), *Agrobacterium*-mediated transformation (Hinchee et al., 1988), direct gene transfer (Paszkowski et al., 1984), and ballistic particle acceleration using devices available from Agracetus, Inc., Madison, Wis. And BioRad, Hercules, Calif. (see, for example, Sanford et al., U.S. Pat. No. 4,945,050; and McCabe et al., 1988). Also see, Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1988 (maize); Fromm et al., 1990 (maize); and Gordon-Kamm et al., 1990 (maize); Svab et al., 1990 (tobacco chloroplast); Koziel et al., 1993 (maize); Shimamoto et al., 1989 (rice); Christou et al., 1991 (rice); European Patent Application EP 0 332 581 (orchardgrass and other Pooideae); Vasil et al., 1993 (wheat); Weeks et al., 1993 (wheat). In one embodiment, the protoplast transformation method for maize is employed (European Patent Application EP 0 292 435, U.S. Pat. No. 5,350,689).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., 1990; Staub et al., 1992). This resulted in stable homoplasmic transformants at a frequency of approximately one per 100 bombardments of target leaves. The presence of cloning sites between these markers allowed creation of a plastid targeting vector for introduction of foreign genes (Staub et al., 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab et al., 1993). Other selectable markers useful for plastid transformation are known in the art and encompassed within the scope of the invention. Typically, approximately 15–20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known.

For example, vectors are available for transformation using *Agrobacterium tumefaciens*. These typically carry at least one T-DNA border sequence and include vectors such as pBIN19 (Bevan, 1984). In one preferred embodiment, the expression cassettes of the present invention may be inserted into either of the binary vectors pCIB200 and pCIB2001 for use with *Agrobacterium*. These vector cassettes for *Agrobacterium*-mediated transformation wear constructed in the following manner. PTJS75kan was created by NarI digestion of pTJS75 (Schmidhauser & Helinski, 1985) allowing excision of the tetracycline-resistance gene, followed by insertion of an AccI fragment from pUC4K carrying an NPTII (Messing & Vierra, 1982; Bevan et al., 1983; McBride et al., 1990). XhoI linkers were ligated to the EcoRV fragment of pCIB7 which contains the left and right T-DNA borders, a plant selectable nos/nptII chimeric gene and the pUC polylinker (Rothstein et al., 1987), and the XhoI-digested fragment was cloned into SalI-digested pTJS75kan to create pCIB200 (see also EP 0 332 104, example 19). PCIB200 contains the following unique polylinker restriction sites: EcoRI, SstI KpnI, BglI, XbaI, and SalI. The plasmid pCIB2001 is a derivative of pCIB200 which was created by the insertion into the polylinker of additional restriction sites. Unique restriction sites in the polylinker of pCIB2001 are EcoRI, SstI, KpnI, BglIII, XbaI, SalI, MluI, BclI, AvrII, ApaI, HpaI, and StuI. PCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the CriT and OriV functions also from RK2. The pCIB2001 polylinker is suitable for the cloning of plant expression cassettes containing their own regulatory signals.

An additional vector useful for Agrobacterium-mediated transformation is the binary vector pCIB 10, which contains a gene encoding kanamycin resistance for selection in plants, T-DNA right and left border sequences and incorporates sequences from the wide host-range plasmid pRK252 allowing it to replicate in both E. coli and Agrobacterium. Its construction is described by Rothstein et al., 1987. Various derivatives of pCIB10 have been constructed which incorporate the gene for hygromycin B phosphotransferase described by Gritz et al., 1983. These derivatives enable selection of transgenic plant cells on hygromycin only (pCIB743), or hygromycin and kanamycin (pCIB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan et al., 1983), the bar gene which confers resistance to the herbicide phosphinothricin (White et al., 1990, Spencer et al., 1990), the hph gene which confers resistance to the antibiotic hygromycin (Blochinger & Diggelmann), and the dhfr gene, which confers resistance to methotrexate (Bourouis et al., 1983).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the E. coli GUS gene and the CaMV 35S transcriptional terminator and is described in the PCT published application WO 93/07278, herein incorporated by reference. One gene useful for conferring resistance to phosphinothricin is the bar gene from Streptomyces viridochromogenes (Thompson et al., 1987). This vector is suitable for the cloning of plant expression cassettes containing their own regulatory signals.

An additional transformation vector is pSOG35 which utilizes the E. coli gene dihydrofolate reductase (DHFR) as a selectable marker conferring resistance to methotrexate. PCR was used to amplify the 35S promoter (about 800 bp), intron 6 from the maize Adhl gene (about 550 bp) and 18 bp of the GUS untranslated leader sequence from pSOG10. A 250 bp fragment encoding the E. coli dihydrofolate reductase type 11 gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG19 and pSOG35 carry the pUC-derived gene for ampicillin resistance and have HindIII, SphI, PstI and EcoRI sites available for the cloning of foreign sequences.

V. Production and Characterization of Stably Transformed Plants

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently. the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer et al., 1992; Laursen et al., 1994) indicating stable inheritance of the gene. The nonchimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

VI. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, ultilane breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

VII. A Computer Readable Medium

The invention also provides a computer readable medium having stored thereon a data structure containing nucleic acid sequences having at least 70% sequence identity to SEQ ID NO:1, as well as complementary, ortholog, and variant sequences thereof. Storage and use of nucleic acid sequences on a computer readable medium is well known in the art. (See for example U.S. Pat. Nos. 6,023,659; 5,867, 402; 5,795,716) Examples of such medium include, but are not limited to, magnetic tape, optical disk, CD-ROM, random access memory, volatile memory, non-volatile memory and bubble memory. Accordingly, the nucleic acid sequences contained on the computer readable medium may be compared through use of a module that receives the sequence information and compares it to other sequence information. Examples of other sequences to which the nucleic acid sequences of the invention may be compared include those maintained by the National Center for Biotechnology Information (NCBI)(available on the World Wide Web at ncbi.-nlm.nih.gov/) and the Swiss Protein Data Bank. A computer is an example of such a module that can read and compare nucleic acid sequence information. Accordingly, the invention also provides the method of comparing a nucleic acid sequence of the invention to another sequence. For example, a sequence of the invention may be submitted to the NCBI for a Blast search as described herein where the sequence is compared to sequence information contained within the NCBI database and a comparison is returned. The invention also provides nucleic acid sequence information in a computer readable medium that allows the encoded polypeptide to be optimized for a desired property. Examples of such properties include, but are not limited to, increased or decreased: thermal stability, chemical stability, hydrophylicity, hydrophobicity, and the like. Methods for the use of computers to model polypeptides and polynucleotides having altered activities are well known in the art and have been reviewed. (Lesyng et al., 1993; Surles et al., 1994; Koehl et al., 1996; Rossi et al., 2001).

VIII. Inhibition of Expression of the Cap Binding Protein 80 Gene

A. Antisense Technology

A number of methods can be used to inhibit the expression of genes encoding cap binding protein 80 in plants. For instance, antisense technology can be conveniently used. To accomplish this, a nucleotide sequence from the desired gene is cloned and operably linked to a promoter such that the antisense strand of RNA is transcribed. Preferably, the promoter is one which drives expression specifically in leaf cells. More preferably, the promoter drives expression specifically in guard cells. The construct is then transformed into plants and the antisense strand of RNA is produced. In plant cells, it has been suggested that antisense suppression can act at all levels of gene regulation including suppression of RNA translation (see, Bourque, 1995; Pantopoulos, 1989; Heiser et al. 1997) and by preventing the accumulation of mRNA which encodes the protein of interest (see, Baulcombe, 1996; Prins and Goldbach, 1996; Metzlaff et al., 1997; Sheehy et al., 1988, and U.S. Pat. No. 4,801,340).

The nucleotide sequence to be introduced generally will be substantially identical to at least a portion of the endogenous cap binding protein 80 gene or other genes to be repressed. The sequence, however, need not be perfectly identical to inhibit expression. The constructs of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about the full-length sequence should be used, though a sequence of at least about 100 nucleotides is preferred, a sequence of at least about 200 nucleotides is more preferred, and a sequence of about 700 to about 3000 nucleotides is especially preferred.

A number of gene regions can be targeted to suppress cap binding protein 80 gene expression. The targets can include, for instance, the coding regions, introns, sequences from exon/intron junctions, 5' or 3'untranslated regions, and the like.

Inhibiting the expression of cap binding protein 80 results in inhibition of the enzyme's activity. It may be desirable to inhibit expression in a way which targets the inhibition to guard cells or to other selected cell types in which the inhibition of cap binding protein 80 is desired. This can be done, for example, by using a promoter which is preferentially or primarily expressed in the cell type of interest.

B. Co-suppression and Double Stranded RNA Gene Silencing

Several techniques have recently been developed for blocking or suppressing the expression of endogenous genes by introduction of exogenous nucleic acids. One well known method of suppression is sense co-suppression. Introduction of nucleic acid configured in the sense orientation has been recently shown to be an effective means by which to block the transcription of target genes. For examples of the use of this method to modulate expression of endogenous genes see, for example, Assaad et al., 1993; Flavell, 1994; Stam et al., 1997 Napoli et al., 1990; and U.S. Pat. Nos. 5,034,323, 5,231,020, and 5,283,184. Post-transcriptional gene silencing induced by introduction of transgenes blocks expression of endogenous genes homologous to the transgene and is thought to be involved in virus resistance and genome maintenance. See, e.g., Cogoni and Macino, 1992. The suppressive effect may occur where the introduced sequence contains no coding sequence per se, but only intron or untranslated sequences homologous to sequences present in the primary transcript of the endogenous sequence.

The-introduced sequence generally will be substantially identical to the endogenous sequence intended to be repressed. This minimal identity will typically be greater than about 65%, but a higher identity might exert a more effective repression of expression, e.g., about 95% to absolute identity is preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

In a further approach to blocking expression of endogenous genes, it has been found that RNA capable of forming duplexes of sense and antisense strands suppresses expression of endogenous genes more powerfully than does introduction of either strand individually in organisms as diverse as plants and worms. See, e.g., Waterhouse et al., 1998; Fire et al., 1998. Post-transcriptional gene silencing by introduction of double stranded RNA therefore provides another powerful tool for inhibiting cap binding protein 80 activity.

C. Triplex DNA Formation

Oligonucleotide-based triple-helix formation can also be used to disrupt cap binding protein 80 gene expression. Triplex DNA can inhibit DNA transcription and replication, generate site-specific mutations, cleave DNA, and induce homologous recombination (see, e.g., Havre and Glazer, 1993; Scanlon et al., 1995; Giovannangeli et al., 1996; Chan and Glazer, 1997. Triple helix DNAs can be used to target the same sequences identified for antisense regulation.

D. Ribozymes

Catalytic RNA molecules or ribozymes can also be used to inhibit expression of cap binding protein 80 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation. In preferred embodiments, the ribozymes are targeted to specific cell types, such as guard cells or leaf cells. Conveniently, this can be achieved by introducing a DNA construct with a promoter specific for the cell type of interest.

A number of classes of ribozymes have been identified. One class of ribozymes is derived from a number of small circular RNAs which are capable of self cleavage and replication in plants. The RNAs replicate either alone (viroid RNAs) or with a helper virus (satellite RNAs). Examples include RNAs from avocado sunblotch or viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, 1993 Eastham and Ahlering, 1996; Sokol and Murray, 1996; Sun et al., 1997; and Haseloff et al., 1988.

E. Modification and Knocking Out of Endogenous Genes

In addition to blocking expression of endogenous genes, as discussed above, methods for introducing genetic mutations into the genes can also be used to select for plants with decreased cap binding protein 80 expression. In preferred embodiments, endogenous genes encoding cap binding protein 80 are modified by, for example, replacing the promoter with a promoter with lower activity, or with an inducible promoter so that expression of the gene can be turned off when conditions warrant.

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N ethylurea. Alternatively, ionizing radiation from sources such as, X-rays or gamma rays can be used.

Alternatively, homologous recombination can be used to induce targeted gene modifications by specifically targeting the cap binding protein 80 gene in vivo (see, generally, Grewal and Klar, 1997; Xu et al., 1996). Homologous recombination has been demonstrated in plants (Puchta et al., 1994, Swoboda et al., 1994; Offtinga et al., 1993; and Kempin et al., 1997).

In applying homologous recombination technology to cap binding protein 80 genes, mutations in selected portions of a cap binding protein 80 gene sequence (including 5' upstream, 3' downstream, and intragenic regions) are made in vitro and then introduced into the desired plant using standard techniques. Since the efficiency of homologous recombination is known to be dependent on the vectors used, use of dicistronic gene targeting vectors as described by Mountford et al. (1994) and Vaulont et al. (1995) may be conveniently used to increase the efficiency of selecting for altered cap binding protein 80 gene expression in transgenic plants. The mutated gene interacts with the target wild-type gene in such a way that homologous recombination and targeted replacement of the wild-type gene occurs in transgenic plant cells, resulting in suppression of cap binding protein 80 activity.

Alternatively, oligonucleotides composed of a contiguous stretch of RNA and DNA residues in a duplex conformation with double hairpin caps on the ends can be used. The RNA/DNA sequence is designed to align with the sequence of the target cap binding protein 80 gene and to contain the desired nucleotide change. Introduction of the chimeric oligonucleotide on an extrachromosomal T-DNA plasmid results in efficient and specific cap binding protein 80 gene conversion directed by chimeric molecules in a small number of transformed plant cells. This method is described in Cole Strauss et al. (1996) and Yoon et al. (1996).

Finally, endogenous genes can also be "knocked-out" by transposons or T-DNA insertion. These are random insertions into the genome that disrupt the activity of the endogenous gene into which the transposon or T-DNA is inserted. Since the insertions are random, the subject cells or plants are then screened for those in which cap binding protein 80 activity has been reduced.

F. Other Means for Inhibiting can Binding Protein 80 Activity

Cap binding protein 80 activity may be modulated by eliminating the proteins that are required for cap binding protein 80 cell-specific gene expression. Thus, expression of regulatory proteins, or the sequences that control cap binding protein 80 gene expression, or both, can be modulated using the methods described here.

Another strategy is to inhibit the ability of a cap binding protein 80 protein to interact with other proteins. This can be achieved, for instance, using antibodies specific to cap binding protein 80. In this method, cell-specific expression of cap binding protein 80-specific antibodies is used to inactivate functional domains through antibody: antigen recognition (see, Hupp et al., 1995). Interference of activity of a cap binding protein 80 interacting protein can be applied in a similar fashion.

Alternatively, dominant negative mutants of cap binding protein 80 can be prepared by expressing a transgene that encodes a truncated cap binding protein 80 protein. Use of dominant negative mutants to inactivate target genes in transgenic plants is described in Mizukami et al. (1996).

In yet another strategy, a peptide, peptidomimetic, or other small molecule inhibitor of cap binding protein 80, i.e., an exogenously applied inhibitor, may be identified. Inhibitors may be tested for and screened by routine assays known in the art. For example, cap binding protein 80 may be expressed in plant cells in vitro, and inhibitors applied to a culture of cells. Inhibition of cap binding protein 80 may be analyzed by the "biochemical" and/or "molecular biological" assays referred to above. The in vivo analysis of a cap binding protein 80 inhibitor may also be conducted, e.g., by applying an inhibitor to a plant and determining if it is effective in inhibiting cap binding protein 80 in a plant of interest using assays known to the art. An effective inhibition of cap binding protein 80 in a plant cell or plant preferably results in a decreased level of cap binding protein 80 expression, an increased level of ABA, increased anion channel activity, increased drought tolerance, decreased stomatal opening or frequency, or any combination thereof.

Peptide, peptidomimetic, or other cap binding protein 80 inhibitors can be exogenously applied to the plants. Conveniently, this can be done by adding the inhibitors to irrigation water or to water or to foliar sprays. Inhibitors can be applied alone or in mixture with other plant hormones, fertilizers, pesticides or fungicides. The inhibitor can be applied in a mixture with a carrier or, if necessary, other auxiliary agents to form any one of the standard types of preparations commonly used in agriculture, for example, a dry blend, granules, a wettable powder, an emulsion, an aqueous solution and the like. Suitable solid carriers are clay, talc, kaolin, bentonite, terra abla, calcium carbonate, diatomaceous earth, silica, synthetic calcium silicate, kieselguhr, dolomite, powdered magnesia, Fuller's earth, gypsum and the like. Solid compositions also can be in the form of dispersible powders or grains, comprising, in addition to the inhibitor, a surfactant to facilitate the dispersion of the powder or grains in liquid. Liquid compositions include solutions, dispersions or emulsions containing the auxins together with one or more surface-active agents such as wetting agents, dispersing agents, emulsifying agents, or suspending agents. In those applications in which the compounds are applied as a foliar spray, surface-active agents are preferably used. Generally, any number of surfactants may be used consistent with the purpose of this constituent. For example the surfactant can comprise a nonionic, anionic, cationic, or zwitterionic surfactant. The surfactant can be formulated with the inhibitor as formulated or, alternatively, the surfactants can be introduced during application to the plant. In such an instance, regardless of whether the application is conducted via automated or manual means, the surfactant can be combined with the inhibitor prior to application or codispensed separately during application. The average molecular weight of useful surfactants ranges from about 100 to about 4000. Cationic surfactants useful in compositions of the invention include, for example, amine ethoxylates, amine oxides, mono- and diilkylamines, imidazolinium derivatives, and alkylbenzyldimethylammonium halides. Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Anionic surfactants useful with the invention comprise, for example, alkyl carboxylates, linear alkylbenzene sulfonates, paraffin sulfonates and secondary n7 alkane sulfonates, sulfosuccinate esters and sulfated linear alcohols. Zwitterionic or amphoteric surfactants useful with the invention comprise a-N-alkylaminopropionic acids, n-alkyl-α-iminodipropionic acids, imidazoline carboxylates, amine oxides, sulfobetaines and sultaines. Although the surfactant can be present in the composition in any useful amount, in preferred embodiments, it is present in an amount from about 0.1% to about 25%, more preferably from about 0.1% to about 10% and more preferably still from about 0.5% to about 5%. A surfactant is present in the compositions of the invention in a useful amount when it facilitates the dissolution of the inhibitor, or enhances its uptake by the plant, or both, or its effectiveness in inducing the desired response, or provides all three of these effects. Compositions used in the methods of the invention can also contain suspending agents. Suitable suspending agents are, for example, hydrophilic colloids, for example polyvinylpyrollidone and sodium carboxymethylcellulose, and vegetable gums, such as gum acacia and gum tragacanth. Aqueous solutions, dispersions or emulsions may be prepared by dissolving the inhibitor in water or an organic solvent which can, if desired, contain one or more surface active, sticking, wetting, dispersing, or emulsifying agents. Suitable organic solvents are, for example, alcohols, hydrocarbons, oils and sulfoxides. In embodiments using alcohols, methanol, isopropyl alcohol, propylene glycol and diacetone alcohol are preferred. In embodiments using oils, petroleum oils are preferred. Of the sulfoxides, dimethylsulfoxide is preferred.

The inhibitor can also be microencapsulated. Microcapsules containing the desired inhibitor can be prepared by co-acervation; or, more preferably, by stirred interfacial polymerization, e.g., an isocyanate/diamine system. The resulting microcapsules may be used as an aqueous suspension. Inhibitors which are to be used in the form of aqueous solutions, dispersions or emulsions are generally supplied in the form of a concentrate containing a high proportion of the inhibitor, and the concentrate is then diluted with water before use. These concentrates are usually required to withstand storage for prolonged periods and after such storage, to be capable of dilution with water in order to form aqueous preparations which remain homogeneous for a sufficient time to enable them to be applied by conventional spray equipment. In general, concentrates can conveniently contain from 10–60 percent by weight of the inhibitor. Dilute preparations ready for use may contain varying amounts of the inhibitor. The practitioner can observe plants treated with the inhibitor and decrease the dilution of the inhibitor if it appears the plants are showing signs of wilting or browning.

In carrying out the methods of the invention, an "effective amount" of a cap binding protein 80 inhibitor is applied to the plants. One of skill will recognize that an effective amount of an inhibitor will vary and will depend upon a number of factors including, for example, the particular inhibitor and formulation selected for use, the timing of the application, whether the compound is to be applied for foliar or root uptake, and the plant species whose growth is to be regulated.

The invention will be further described by the following examples which are not intended to limit the scope of the invention.

EXAMPLE 1

Isolation of an *Oryza sativa* Cap Binding Protein 80 (OsCBP80) Gene

It had been reported that a knock out of the *Arabidopsis* CBP80 gene resulted in a plant that had altered hormone signaling, reduced stomatal opening and/or enhanced anion channel activation. Based upon available human CBP80 sequences, *Arabidopsis* CBP80 sequences in a public database were identified. The *Arabidopsis* CBP80 sequence was then used to identify contigs in a rice database having CBP80 sequences. Four contigs were identified and oligonucleotide primers (primers 1–15 corresponding to SEQ ID NOs: 3–17) were designed based on the sequences in those contigs. Various primer pairs were used in a polymerase chain reaction (PCR) to amplify cDNAs encoding rice CBP80 from a rice root cDNA library. The reaction conditions were 94° C. for 3 minutes; then 35 cycles of 94° C. for 0.5 minute and 70° C. for 2.5 minutes; then 4° C. Products were sequenced and a subsequent PCR performed to obtain a full-length clone from the rice root library.

The DNA sequence of the full-length rice CBP80 open reading frame (ORF) and the amino acid sequence of the encoded polypeptide is shown in SEQ ID NOs:1 and 2, respectively. The ORF begins at position 82 and ends at position 2688 of the DNA shown in SEQ ID NO:1. As maize, wheat and banana have sequences with some similarity to SEQ ID NO:1 or 2, those sequence are useful to isolate orthologs of rice CBP80. Those sequences include SEQ ID Nos: 21–54.

As CBP80 is likely involved in ABA signaling, the rice CBP80 full-length DNA or portions thereof are useful to prepare constructs for over or under expression, or knock outs, or to modify the nucleic acid sequence so as to encode a CBP80 protein with modified function, i.e., a dominant negative mutant or a polypeptide lacking or having reduced activity.

Transgenic plants having these constructs have reduced or decreased, or lack, expression of endogenous CBP80, which leads to alterations in ABA signaling. The alterations in ABA signaling are characterized by reduced stomatal opening and reduced water loss, i.e., the transgenic plants have enhanced drought tolerance.

EXAMPLE 2

CBP80 Vectors

Overexpression Vectors

Vectors used for expression of full-length genes of interest in plants (overexpression) are designed to overexpress the protein of interest and are of two general types, biolistic and binary, depending on the plant transformation method to be used.

For biolistic transformation, biolistic vectors include i) a backbone with a bacterial selectable marker (typically, an antibiotic resistance gene) and an origin of replication functional in *Escherichia coli* (*E. coli*; e.g., ColE1), and ii) a plant-specific portion including a gene expression cassette comprising a promoter (e.g., ZmUBlint MOD), the gene of interest (typically, a full-length cDNA) and a transcriptional terminator (e.g., the *Agrobacterium tumefaciens* nos terminator), and a plant selectable marker cassette comprising a promoter (e.g., rice ActID-BV MOD), a selectable marker gene (e.g., phosphomannose isomerase, PMI) and a transcriptional terminator (e.g., CaMV terminator).

Vectors for transformation by *Agrobacterium tumefaciens* (*A. tumefaciens*; binary vectors) include i) a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene, and ii) a plant-specific portion as described above for biolistic vectors except that this portion is flanked by *A. tumefaciens* right and left border sequences which mediate transfer of the DNA flanked by these two sequences to the plant.

Knock Out Vectors

Vectors designed for reducing or abolishing expression of a single gene or of a family of related genes (knock out vectors) are also of two general types corresponding to the methodology used to downregulate gene expression: antisense or double-stranded RNA interference (dsRNAi).

Antisense Vectors

For antisense vectors, a full-length or partial gene fragment (typically, a portion of the cDNA) can be used in the same vectors described for full-length expression, as part of the gene expression cassette. For antisense-mediated downregulation of gene expression, the coding region of the gene or gene fragment is in the opposite orientation relative to the promoter; thus, mRNA corresponds to the non-coding (antisense) strand in planta.

dsRNAi Vectors

For dsRNAi vectors, a partial gene fragment (typically, 300 to 500 basepairs long) is used in the gene expression cassette, and is expressed in both the sense and antisense orientations, separated by a spacer region (typically, a plant intron, e.g., the OsSH1 intron 1, or a selectable marker, e.g., one conferring kanamycin resistance). Vectors of this type are designed to form a double-stranded mRNA stem, resulting from the basepairing of the two complementary gene fragments in planta.

Biolistic or binary vectors designed for overexpression or knock out can vary in a number of different ways, including the selectable markers used in plants and bacteria, the transcriptional terminators used in the gene expression and plant selectable marker cassettes, the methodologies used for cloning gene or gene fragments of interest (typically, conventional restriction enzyme-mediated or Gateway™ recombinase-based cloning) and the nature of the gene expression cassette promoter driving expression of the gene or gene fragment of interest. For example, the promoter may drive expression in most tissues of the plants (constitutive, e.g., ZmUBIint MOD), in specific plant tissues (e.g., maize ADP-gpp for endosperm-specific expression), or in an inducible fashion (e.g., GAL4bsBzl for estradiol-inducible expression in lines constitutively expressing the cognate transcriptional activator for this promoter).

For example, a rice CBP80 cDNA or a fragment thereof is subcloned using conventional restriction enzyme-based cloning into a vector, downstream of the maize ubiquitin promoter and intron, and upstream of the *Agrobacterium tumefaciens* nos 3' end transcriptional terminator. The resultant gene expression cassette is further subcloned, using conventional restriction enzyme-based cloning, into the pNOV2117 binary vector, generating pNOVCBP80.

The pNOVCBP80 binary vector is designed for transformation and overexpression of CBP80 in monocots. The vector including a binary backbone containing the sequences necessary for selection and growth in *Escherichia coli* DH-5α (Invitrogen) and *Agrobacterium tumefaciens* LBA4404, including the bacterial spectinomycin antibiotic resistance aadA gene from *E. coli* transposon Tn7, origins of replication for *E. coli* (ColE1) and *A. tumefaciens* (VS1), and the *A. tumefaciens* vir gene. In addition to the binary backbone, pNOV2117 contains the T-DNA portion flanked by the right and left border sequences, and including the Positech™ (Syngenta) plant selectable marker and the CBP80 gene expression cassette. The Positech™ plant selectable marker confers resistance to mannose via a cassette including the maize ubiquitin promoter driving expression of the PMI (phosphomannose isomerase) gene followed by the CMV transcriptional terminator.

pNOVCBP80 is transformed into a rice cultivar (Kaybonnet) using *Agrobacterium*-mediated transformation, and mannose-resistant calli are selected and regenerated. *Agrobacterium* is grown on YPC solid plates for 2–3 days prior to experiment initiation. Agrobacterial colonies are suspended in liquid MS media to an OD of 0.2 at λ600 nm. Acetosyringone is added to the agrobacterial suspension to a concentration of 200 μM and the bacteria are induced for 30 minutes.

Three-week-old calli which are induced from the scutellum of mature seeds in the N6 medium (Chu et al., 1975) are incubated in the *Agrobacterium* solution in a 100×25 petri plate for 30 minutes with occasional shaking. The solution is then removed with a pipet and the callus transferred to a MSAs medium which is overlayed with sterile filter paper. Cocultivation is continued for 2 days in the dark at 22° C. Calli are then placed on MS-Timetin plates for 1 week, after which they are transferred to PAA+ mannose selection media for 3 weeks. Growing calli are picked and transferred to PAA+ mannose media and cultivated for 2 weeks in light.

Colonies are transferred to MS20SorbKinTim regeneration media in plates for 2 weeks in light. Small plantlets are transferred to MS20SorbKinTim regeneration media in GA7 containers. When they reach the lid, they are transferred to soil in the greenhouse.

Alternatively, plasmid pCIB7613, which contains the hygromycin phosphotransferase (hpt) gene as a selectable marker, may be employed for transformation. Other useful plasmids include pNADII002 (GALA-ER-VP16) which contains the yeast GALA DNA Binding domain (Keegan et al., 1986), the mammalian estrogen receptor ligand binding domain (ER; Greene et al., 1986)) and the transcriptional activation domain of the HSV VP16 protein (Triezenberg et al., 1988). Both hpt and GAIA-ER-VP16 are constitutively expressed using the maize Ubiquitin promoter, and pSGCDL1 (GAL4BS Bzl Luciferase), which carries the firefly luciferase reporter gene under control of a minimal maize Bronzel (Bzl) promoter with 10 upstream synthetic GALA binding sites. All constructs use termination signals from the nopaline synthase gene.

*Oryza sativa* L. Japonica CV. Taipei 309 is used for the production of transgenic rice plants. Callus induction, cell suspension, initiation, and maintenance follow protocols previously described by Zhang (1995). Gene transfer is achieved using the Biolistic PDS-1000 system (Bio-Rud. Hercules, Calif.). pCIB7613 is co-transferred with other plasmids in a 1:5 molar ratio. DNA coating, high-velocity microprojectile delivery of DNA, selection, and regeneration of transgenic plants are achieved according to Zhang et al. (1998) and Chen et al. (1998a).

Estradiol (Sigma) is resuspended in 95% ethanol and diluted in water containing 0.01% Triton X-100 immediately before use. The same volume of 95% ethanol is added to the negative control solution without estradiol. Approximately ten-milligram samples of fresh plant tissue are excised and submerged in estradiol solution, and cultured at 25° C. without light. In whole-plantlet treatments, either intact plantlets are submerged in 1 μM estradiol solution and cultured at 25° C. in dark for 24 hours, or plantlet roots are submerged in ½ MS salts (Murashige and Skoog, 1962) liquid medium containing estradiol followed by incubation at 25° C. with 16 hour light cycles.

Expression of the CBP80 in transgenic $T_0$ plants is analyzed. Additional rice cultivars, including but not limited to, Nipponbare, Taipei 309 and Fuzisaka are also transformed and assayed for expression of the CBP80 product and enhanced protein expression.

REFERENCES

Aarts et al., *Proc Natl Acad Sci* 95:10306 (1998).
Alonso et al., *Science*, 284:2148 (1999)
Altschul et al., *J. Mol. Biol.*, 215:403 (1990).
Altschul et al., *Nucleic Acids Res.*, 25:3389 (1997).
An et al., *EMBO J.* 4:277 (1985).
Aoyama et al., *N-H Plant Journal*, 11:605 (1997).
Assaad et al., *Plant Mol. Bio.*, 22:1067 (1993).
Bachem et al., *Plant J.*, 2:745 (1996).
Bailey and Elkan In: Proceedings of the second international Conference on Intelligent Systems for Molecular Biology (Altman, R., ed), pp 28–36, AAAI press (1994).
Ballas et al., *Nucleic Acids Res.*, 17:7891 (1989).
Balzi et al., *J. Biol. Chem.*, 62:2206 (1994).
Bansal et al., *Proc. Natl. Acad. Sci. USA*, 89:3654 (1992).
Barnett et al., *Plant Physiol.*, 41:1222 (1966).
Batzer et al., *Nucleic Acid Res.*, 19:5081 (1991).
Baulcombe, *Plant Mol. Bio.*, 32:79 (1996).
Beachy and Murakishi, *Phytopathology*, 61:877 (1971).
Beals et al., *Plant Cell*, 9:1527 (1997).
Belanger et al., *Genetics*, 129:863 (1991).
Bevan et al., *Nucl. Acids Rles.*, 11:369 (1983).
Bevan et al., *Nature*, 304:184 (1983).
Bird et al., *Plant Molecular Biology*, 11:651 (1988).
Blochlinger & Diggelmann, *Mol Cell Biol*, 4:2929 (1984).
Bouchez et al., *EMBO Journal*, 8:4197 (1989).
Bourouis et al., *EMBO J.*, 2:1099 (1983).
Bourque, *Plant Sci. (Limerick)*, 105:125 (1995).
Boyer, *Water deficits and plant growth*, T. T. Kozlowski (ed.)., Academic Press, New York., pp. 154–190 (1976).
Boyes et al., *Proc Natl Acad Sci USA*, 95:15849 (1998).
Byrne et al. *Plant Cell Tissue and Organ Culture*, 8:3 (1987).
Campbell and Gowri, *Plant Physiol.*, 92:1 (1990).
Canto and Palukaitis, *Virology*, 265:74 (1999).
Cao et al., *Cell*, 88:57 (1997).
Cao et al., *Plant Cell*, 6:1583 (1994).
Century et al., *Science*, 278:1963 (1997).
Chan and Glazer, *J. Mol. Medicine (Berlin)*, 75: 267 (1997).
Chandler et al., *Plant Cell*, 1:1175 (1989).
Chen et al., *Nature Biotechnology*, 16:1060 (1998).
Christou et al., *Biotechnology*, 9:957 (1991).
Christou et al., *Plant Physiol.*, 87:671 (1988).
Chu et al., *Sci. Sin.*, 18:659 (1975).
Cogoni and Macino, *Nature*, 399:166 (1999).
Cole-Strauss et al., *Science*, 273:1386 (1996).
Colot et al., *Genes Dev.*, 10:1699 (1996).
Conklin and Last, *Plant Physiol.*, 109:203 (1995).
Cooper et al., *Virology*, 206:307 (1995)
Cooper et al., *Virology*, 216:208 (1996).
Cordero et al., *Plant J.*, 6:141 (1994).
Corpet et al., *Nucleic Acids Res.* 16:10881 (1988).
Crameri et al., *Nature Biotech.*, 15:436 (1997).
Crameri et al., *Nature*, 391:288 (1998).
Creelman et al., *Annu Rev Plant Physiol Plant Mol Biol* 48:355 (1997).
Creighton, *Proteins*, W. H. Freeman and Company (1984).
Crossway et al., *BioTechniques*, 4:320 (1986).
Czako et al., *Mol. Gen. Genet.*, 235 (1):33 (1992).
Czernic et al., *Plant Mol. Biol.*, 31:255 (1996).
Datia et al., *Bio/Technology*, 8:736 (1990).
Dayhoff et al., *Atlas of Protein Sequence and Structure*, Natl. Biomed. Res. Found., Washington, C.D. (1978).
De Blaere et al., *Meth. Enzymol.* 143:277 (1987).
de Framond, *FEBS*, 290:103 (1991).
De Oliveira et al., *Microbios.*, 76:213 (1993).
Delaney et al., *Proc. Natl. Acad. Sci. USA* 92:6602 (1995).
Della-Cioppa et al., *Plant Physiology*, 84:965 (1987).
Dennis et al., *Nucleic Acids Res.*, 12:3983 (1984).
Diekman & Fischer, *EMBO*, 7:3315 (1988).
Dong et al., *Curr Opin Plant Biol* 1:316 (1998).
Dunigan and Madlener, *Virology*, 207:460 (1995).
Durrant et al., *The Plant Cell*, L2:963 (2000).
Dzelkalns et al., *Plant Cell*, 5:855 (1993).
Eastham and Ahlering, *J. Urology*, 156, 1186 (1996).
Eisen et al., *Trends in Plant Sci.* 95:14863 (2000).
Ellis and Jones, *Curr Opin Plant Bio* 1:288 (1998).
Ellis et al., *EMBO Journal*, 6:3203 (1987).
Elroy-Stein et al., *Proc. Natl. Acad. Sci. U.S.A.*, 86:6126 (1989).
English, et al., *Plant Cell* 8:179 (1996).
Eulgem et al., *Trends in Plant Sci.* 5:199 (2000).
Falk et al., *Proc Natl Acad Sci USA* 96:3292 (1999).
Feys et al., *Plant Cell* 6:751 (1994).
Fire et al., *Nature* 391:806 811 (1998).
Flavell. *Proc. Natl. Acad. Sci. U.S.A.*, 91: 3490 (1994).
Franken et al., *EMBO J.*, 10:2605 (1991).
Fromm et al., *Bio/Technology*, 8:833 (1990).
Gallie et al., *Molecular Biology of RNA*, 237 (1989).
Gallie et al., *Nucl. Acids Res.*, 15:8693 (1987).
Gallie, et al., *The Plant Cell*, 1:301 (1989).
Gan et al., *Science*, 270:1986 (1995).
Gatz *Current Opinion in Biotechnology*, 7:168 (1996).
Gatz, C., *Annu. Rev. Plant Physiol. Plant Mol. Biol.*, 48:89 (1997).
Gelfand, eds., *PCR Strategies* (Academic Press, New York (1995)).
Giovannangeli et al., *Biochemistry*, 35:10539 (1996).
Glazebrook et al., *Genetics* 143:973 (1996).
Glazebrook et al., *Proc. Natl. Acad. Sci. USA* 91:8955 (1994).
Glazebrook, J., *Curr. Opin. Plat Biology*, 2:280 (1999).
Gordon-Kamm et al., *Plant Cell*, 2:603 (1990).
Greene et al., *Science*, 231:1150 (1986).
Graham et al., *Biochem. Biophys. Res. Comm.*, 101:1164 (1981).
Graham et al., *J. Biol. Chem.*, 260:6555 (1985).
Graham et al., *J. Biol. Chem.*, 260:6561 (1985).
Grewal and Klar, *Genetics*, 146: 1221 (1997)
Guerineau et al., *Mol. Gen. Genet.* 262:141 (1991).
Gulyas and Farkas, *Phytopath. Z.*, 91:182 (1978)
Hamm and Maataj, *Cell*, 63:109 (1990).
Hammand-Kosack and Jones, *Ann. Rev. Plant Physiol. Plant Mol. Biol.*, 48:575 1997).
Haseloff et al., *Nature*, 334, 585 (1988).
Havre and Glazer, *J. Virology*, 67:7324 (1993).
Heinlein et al., *Science*, 270:1983 (1995).
Heiser et al., *Plant Sci. (Shannon)*, 127: 61 (1997).
Henikoff & Henikoff, *Proc. Natl. Acad. Sci. U.S.A.*, 89:10915 (1989).
Henikoff and Henikoff, *Proc. Natl. Acad. Sci. USA*, 89:10915 (1992).
Hiei et al., *Plant J.*, 6:271 (1994).
Higgins et al., *CABIOS*, 5:151 (1989).
Higgins et al., *Gene*, 73:237 (1988).
Hinchee et al., *Biotechnology*, 6:915 (1988).
Hoekema, In: *The Binary Plant Vector System*. Offset-drukkerij Kanters B.V. (1985).
Horvath and Chua, *Plant Mol. Biol.*, 31:1061 (1996).
Huang et al., *CABIOS*, 8:155 (1992).

Hudspeth & Grula, *Plant Molec. Biol.*, 12:579 (1989).
Huffman et al., *J. Cell. Biochem.*, 17B: Abstract.
Humble et al., *Plant Physiol.*, 48:447 (1971).
Hunt et al., *Mol. Plant-Microbe Int* 9:261 (1997).
Hupp et al., *Cell*, 83:237 (1995).
Imamura, *Jap. J. Bot.*, 12:251 (1943).
Ingelbrecht et al., *Plant Cell*, 1:671 (1989).
Innis and Gelfand, eds., *PCR Methods Manual* (Academic Press, New York) (1999).
Innis et al., eds., *PCR Protocols: A Guide to Methods and Applications* (Academic Press, New York (1995)).
Izaurralde and Matta, *Cell*, 81:153 (1995).
Izaurralde et al., *Cell*, 78:657 (1994).
Izaurralde et al., *J. Cell, Biol.*, 118:1287 (1992).
Jobling et al., *Nature*, 325:622 (1987).
John et al., *Proc. Natl. Acad. Sci. U.S.A.*, 89:5769 (1992).
Jones et al., *Adv Bot Res* 24:89 (1997).
Joshi et al., *Nucleic Acid Res.* 15:9627 (1987).
Joshi, *NAR*, 15:6643 (1987).
Karlin and Altschul, *Proc. Natl. Acad. Sci. U.S.A.*, 87:2264 (1990).
Karlin and Altschul, *Proc. Natl. Acad. Sci. U.S.A.*, 90:5873 (1993).
Keegan et al., *Science*, 231:699 (1986).
Keller et al., *Genes Dev.*, 3:1639 (1989).
Kempin et al., *Nature*, 389:802 (1997).
Klein et al., *Bio/Technology*, 6:559 (1988) (Klein et al. I).
Klein et al., *Nature (London)*, 327:70 (1987).
Klein et al., *Plant Physiol.*, 91:440 (1988) (Klein et al. II).
Klein et al., *Proc. Natl. Acad. Sci. U.S.A.*, 85:4305 (1988) (Klein et al. III).
Knauf, et al., Genetic Analysis of Host Range Expression by Agrobacterium In: Molecular *Genetics of the Bacteria-Plant Interaction*, Puhler, A. ed., Springer-Verlag, New York, 245 (1983).
Kohler et al., *Plant Mol. Biol.*, 29:1293 (1995).
Komari, *Plant Cell Reports*, 9:303 (1990).
Koziel et al., *Biotechnology*, 11:194 (1993).
Kridl et al., *Seed Science Research*, 1:209 (1991).
Kriz et al., *Mol. Gen. Genet.*, 207:90 (1987).
Kunkel et al., *Methods in Enzymol.*, 154:367 (1987).
Kunkel, *Proc. Natl. Acad. Sci. U.S.A.*, 82:488 (1985).
Lange et al., *Plant Sci.*, 142:133 (1999).
Langridge et al., *Cell*, 34:1015 (1983).
Langridge et al., *Proc. Natl Acad. Sci. U.S.A.*, 86:3219 (1989).
Lashbrook et al., *Plant Cell*, 6:1485 (1994).
Laursen et al., *Plant Mol. Biol.*, 24:51 (1994).
Leister et al., *P.N.A.S.*, (USA), 95:370 (1998).
Leister et al., *Proc. Natl. Acad. Sci. USA*, 95:370 (1998).
Liang et al., *Science*, 257:967 (1992).
Lin et al., *Nature*, 402:761 (1999).
Lindstrom et al., *Der. Genet.*, 11:160 (1990).
Lindstrom et al., *Der. Genet.*, 11: 160 (1990).
Lommel et al., *Virology*, 81:382 (1991).
Lorz et al. *Mol. Gen. Genet.*, 199:178 (1985).
Ly et al., *Science*, 287:2486 (2000).
Macejak et al., *Nature*, 353:90 (1991).
Mansson et al., *Gen. Genet.* 200:356 (1985).
Martin and Paz-Ares, *Trends in Genetics* 13:67 (1997).
Martinez et al., *J. Mol. Biol.*, 208:551 (1989).
McBride et al., *Proc. Natl. Acad. Sci. U.S.A.*, 91:7301 (1994).
McCabe et al., *Bio/Technology*, 6:923 (1988).
McDowell et al., *Plant Cell* 10:1861 (1998).
McDowell et al., *Plant J.* 22:523 (2000).
McNellis et al., *Plant J.* 1998, 14:247–257.
Meinkoth and Wahl, *Anal. Biochem.*, 138:267 (1984).
Messing & Vierra, *Gene*, 19:259 (1982).
Metzlaff et al., *Cell*, 88: 845 (1997).
Meyers et al., *Plant J.* 20:317 (1999).
Mizukami et al., *Plant Cell*, 8:831 (1996).
Mogen et al., *Plant Cell* 2:1261 (1990).
Moore et al., *J. Mol. Biol.*, 272:336 (1997).
Mountford et al., *Proc. Natl. Acad. Sci. U.S.A.*, 91: 4303 (1994).
Muller-Rober et al., *Plant Cell*, 6:601 (1994).
Munroe et al., *Gene*, 91:151 (1990).
Murray et al., *Nucleic Acids Res.*, 17:477 (1989).
Myers and Miller, *CABIOS*, 4:11 (1988).
Nakamura et al., *Plant Physiol.*, 109:371 (1995).
Napoli et al., *The Plant Cell*, 2:279 (1990).
Needleman and Wunsch, *J. Mol. Biol.*, 48:443 (1970).
Odell et al. *Mol. Gen. Genet.*, 113:369 (1990).
Odell et al., *Nature*, 313:810 (1985).
Offlinga et al., *Proc. Natl. Acad. Sci. U.S.A.*, 90: 7346 (1993).
Ohno et al., *Nucleic Acids Res.*, 18:6989 (1990).
Ohtsuka et al., *J. Biol. Chem.*, 260:2605 (1985).
Okamuro et al., *Biochemistry of Plants*, 15:1 (1989).
Otsuki et al., *Virology*, 50:45 (1972)
Pacciotti et al. *Bio/Technology*, 3:241 (1985).
Padgett and Beachy, *Plant Cell*, 5:577 (1993).
Pantopoulos, in: *Progress in Nucleic Acid Research and Molecular Biology*, Vol. 48. Cohn, W. E. and K. Moldave (Ed.). Academic Press, Inc., San Diego, 18 California, p. 181–238.
Park et al., *J. Plant Biol.*, 38:365 (1985).
Paszkowski et al., *EMBO J.*, 3:2717 (1984).
Pear et al., *Plant Molecular Biology*, 13:639 (1989).
Pearson and Lipman, *Proc. Natl. Acad. Sci.*, 85:2444 (1988).
Pearson et al., *Meth. Mol. Biol.*, 24:307 (1994).
Pei et al., *Science*, 282:287 (1998).
Penninck et al., *Plant Cell* 8:2309 (1996).
Perlak et al., *Proc. Natl. Acad. Sci. U.S.A.*, 88:3324 (1991).
Pieterse et al., *Plant Cell*, 10:1571 (1998).
Pieterse et al., *Plant Cell*, 8:1225 (1996).
Potrykus *Mol. Gen. Genet.*, 199:183 (1985).
Poulsen et al., *Mol. Gen. Genet.*, 205:193 (1986).
Prins and Goldbach, *Arch. Virol.*, 141: 2259 (1996).
Proudfoot, *Cell*, 64:671 (1991).
Publishing Company, New York (1983).
Puchta et al., *Experientia*, 50: 277 (1994).
Quigley et al., *J. Mol. Evol.*, 29:412 (1989).
Ralston et al., *Genetics*, 119:185 (1988).
Rasmussen and Lis, *Proc. Natl. Acad. Sci. U.S.A.*, 90:7923 (1993).
Reina et al., *Nucleic Acids Res.*, 18:6425 (1990).
Reina et al., *Nucleic Acids Res.*, 18:7449 (1990).
Riggs et al., *Proc. Natl. Acad. Sci. U.S.A.*, 83:5602 (1986).
Rommens et al., *Plant Cell*, 2:1537 (1995).
Ronald, *Curr Opin Plant Biol* 1:294 (1998).
Rossolini et al., *Mol. Cell. Probes*, 8:91 (1994).
Roth et al., *Nature Biotechnology*, 16:939 (1998).
Ruiz et al., *Plant Cell* 10:937 (1998).
Ryals et al., *Plant Cell* 8:1809 (1996).
Ryals et al., *Plant Cell* 9:425 (1997)
Salditt-Georgieff et al., *Cell*, 19:69 (1980).
Sambrook et al., *Molecular Cloning: A Laboratory Manual* (2d ed., Cold Spring Harbor Laboratory Press, Plainview, N.Y.) (1989).
Sanchez-Fernandez et al., *Mol. Gen. Genet.*, 258:655 (1998).
Sanfacon et al., *Genes Dev.*, 5:141 (1991).

Sanford et al., *Particulate Science and Technology*, 5:27 (1987).
Scanlon et al., *FASEB J*, 9:1288 (1995).
Schernthaner et al., *EMBO J.*, 7:1249 (1988).
Schindler et al., *Plant Cell* 4:1309 (1992).
Schmitz and Rao, *Virology*, 248:323 (1996)
Schroeder et al., *Nature*, 410:329 (2001).
Schwob et al., *Plant J.*, 4:423 (1993).
Shah et al., *Mol. Plant-Microbe Interact.* 10:69 (1997).
Sheehy et al., *Proc.Nat. Acad. Sci.U.S.A.*, 85:8805 (1988).
Shen et al., *J. Biol. Chem.*, 275:23718 (2000).
Shimamoto et al., *Nature*, 338:274 (1989).
Shirasu et al., *Plant Cell* 9:261 (1997).
Shulaev et al., *Plant Cell* 7:1691 (1995).
Simpson, *Plant Mol. Biol.*, 19:699 (1985).
Skriver and Mundy, *Plant Cell*, 2:503 (1990).
Skuzeski et al., *Plant Molec. Biol.*, 15:65 (1990).
Slater et al. *Plant Mol. Biol.*, 5:137 (1985).
Smart and Fleming, *J. Biol. Chem.*, 271:19351 (1996).
Smith et al., *Adv. Appl. Math.*, 2:482 (1981).
Smith et al., *Planta*, 168:94 (1986).
Sokol and Murray, *Transgenic Res.*, 5, 363 (1996).
Song et al., *Science*, 270:1804 (1995).
Spencer et al., *Theor. Appl. Genet.*, 79:625 (1990).
Starn et al.; *Annals Bot.*, 79: 3 (1997).
Staswick et al., *Proc. Natl. Acad. Sci. USA* 89:6837 (1992).
Slaub et al., *EMBO J.*, 12:601 (1993).
Staub et al., *Plant Cell.* 4:39 (1992).
Stemmer, *Nature*, 370:389 (1994).
Stemmer, *Proc. Natl. Acad. Sci. U.S.A.*, 91:10747 (1994).
Sukhapinda et al. *Plant Mol. Biol.*, 8:209 (1987).
Sullivan et al., *Mol. Gen. Genet.*, 215:431 (1989).
Sun et al., *Mol. Biotechnology*, 7, 241 (1997).
Svab et al., *Proc. Natl. Acad. Sci. U.S.A.*, 87:8526 (1990).
Svab et al., *Proc. Natl. Acad. Sci. U.S.A.* 90:913 (1993).
Swoboda et al., *EMBO J.*, 13: 484 (1994).
Thomma et al., *Plant Physiol.*, 121:1093 (1999).
Thomma et al., *Proc. Natl. Acad. sci. U.S.A.*, 85:15107 (1998).
Tijssen, *Laboratory Techniques in Biochemistry and Molecular Biology—Hybridization with Nucleic Acid Probes*, part I chapter 2 "Overview of principles of hybridization and the strategy of nucleic acid probe assays" Elsevier, New York (1993).
Turner et al., *Molecular Biotechnology*, 3:225 (1995).
Uernera & Jigami, *J. Bacteriol.*, 174:5526 (1992).
Ulmasov et al. *Plant Mol. Biol.*, 35:417 (1997).
VanTunen et al., *EMBO J.*, 7:1257 (1988).
Vasil et al., *Biotechnology*, 11:1553 (1993).
Vaulont et al, *Transgenic Res.*, 4: 247 (1995).
Verduin, *J. Gen. Virol.*, 38:571 (1978).
Vernooij et al., *Plant Cell* 6:959 (1994).
Visa et al., *J. Cell. Biol.*, 133:5 (1996).
Visedo et al., *Physiologia Plantarum*, 78:218 (1990).
Vodkin, *Prog. Clin. Biol. Res.*, 138:87 (1983).
Vogel et al., *EMBO J.*, 11:157 (1992).
Walker and Gaastra, eds., *Techniques in Molecular Biology*, MacMillan publishing Company, New York (1983).
Wandelt et al., *Nucleic Acids Res.*, 17:2354 (1989).
Waterhouse, et al., *Proc. Natl. Acad. Sci. U.S.A.*, 95:13959 (1998).
Waterman; M.S. Introduction to Computational Biology: Maps, sequences and genomes. Chapman & Hall. London (1995).
Weeks et al., *Plant Physiol.*, 102:1077 (1993).
Weissinger et al., *Annual Rev. Genet.*, 22:421 (1988).
Wenzler et al., *Plant Mol. Biol.*, 13:347 (1989).
Weymann et al., *Plant Cell* 7:2013 (1995).
White et al., *Nucl Acids Res*, 18:1062 (1990).
White et al., *Nuc Acids Res*, 18:1062 (1990).
Whitham et al., *Cell*, 78:1101 (1994).
Whitham et al., *P.N.A.S.*, (USA), 93:8776 (1996).
Willits et al., *Mol Plant-Microbe Interact* 11:795 (1998).
Wilson et al., *J. Biol. Chem.*, 274:4166 (1999).
Xie et al., *Science* 280:1091 (1998).
Xu et al., *Genes Dev.*, 10: 2411 (1996).
Yamamoto et al., *Nucleic Acids Res.*, 18:7449 (1990).
Yang & Kiessig, *Proc. Natl. Acad. Sci. USA* 93:14972 (2000).
Yang et al., *Plant Mol. Biol.*, 38:1201 (1998).
Yoon et al., *Proc. Natl. Acad. Sci. U.S.A.*, 93: 2071 (1996).
Yu et al., *Proc. Natl. Acad. Sci. USA* 95:7819 (1998).
Zhang et al., *Plant Cell Reports*, 15:68 (1995).
Zhang et al., *Proc. Natl. Acad. Sci. USA*, 94:4504 (1997).
Zhang et al., *Molecular Breeding*, 4:551 (1998).
Zhao and Pick, *Nature*, 365, 448 (1993).
Zhou et al., *EMBO J.*, 16:3207 (1997).
Zhou et al., *Plant Cell* 10:1021 (1998).
Zhou et al., *Plant Cell* 8:2235 (1996).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated polynucleotide comprising a nucleotide sequence having an open reading frame which encodes a rice cap binding protein 80, which open reading frame comprises nucleotides 82 to 2688 of SEQ ID NO: 1 or the complement thereof.

2. The isolated polynucleotide according to claim 1, wherein the cap binding protein 80 comprises the amino acid sequence of SEQ ID NO:2.

3. An expression cassette comprising the polynucleotide according to claim 1 operably linked to a promoter which drives expression in a plant.

4. The expression cassette according to claim 3 wherein the open reading frame is in antisense orientation relative to the promoter.

5. The expression cassette according to claim 3 wherein the open reading frame is in sense orientation relative to the promoter.

6. A host cell comprising the expression cassette according to claim 3, wherein said host cell is a plant cell or bacterial cell.

7. A transgenic rice plant, comprising the isolated polynucleotide according to claim 1.

8. A transgenic rice plant, comprising the expression cassette according to claim 4.

9. The transgenic rice plant according to claim 7 which is hypersensitive to ABA compared to a wild-type rice plant.

10. The transgenic rice plant according to claim 8 which is hypersensitive to ABA compared to a wild-type rice plant.

11. A recombinant vector comprising the polynucleotide according to claim 1.

12. The recombinant vector according to claim 11 wherein the vector is a plasmid, Ti plasmid, phagemid, cosmid, YAC, BAC, virus, F-factor or phage.

13. An isolated polynucleotide comprising SEQ ID NO. 1.

* * * * *